United States Patent
Grant

(10) Patent No.: US 8,562,344 B2
(45) Date of Patent: Oct. 22, 2013

(54) DENTAL PLATFORM ASSEMBLY AND METHODS

(75) Inventor: James C. Grant, Colorado Springs, CO (US)

(73) Assignee: Grant Dental Technology Corporation, Colorado Springs, CO (US)

(*) Notice: Subject to any disclaimer, the term of this patent is extended or adjusted under 35 U.S.C. 154(b) by 60 days.

(21) Appl. No.: 13/014,526

(22) Filed: Jan. 26, 2011

(65) Prior Publication Data

US 2011/0151408 A1 Jun. 23, 2011

Related U.S. Application Data

(63) Continuation-in-part of application No. 12/694,911, filed on Jan. 27, 2010, now Pat. No. 8,287,278, which is a continuation-in-part of application No. 12/243,676, filed on Oct. 1, 2008, now Pat. No. 8,231,388, which is a continuation-in-part of application No. 12/074,524, filed on Mar. 4, 2008, now Pat. No. 7,806,685.

(51) Int. Cl.
*A61C 8/00* (2006.01)
*A61C 5/00* (2006.01)

(52) U.S. Cl.
USPC .......................................... 433/172; 433/215

(58) Field of Classification Search
USPC ........... 433/172–176, 201.1, 202.2, 215, 220, 433/221, 76; 606/280, 70–71, 281–299, 606/86 B
See application file for complete search history.

(56) References Cited

U.S. PATENT DOCUMENTS

| | | | |
|---|---|---|---|
| 4,086,701 A | | 5/1978 | Kawahara et al. |
| 4,713,003 A | * | 12/1987 | Symington et al. ........... 433/173 |
| 5,018,970 A | * | 5/1991 | Stordahl ......................... 433/75 |
| 5,040,982 A | | 8/1991 | Stefan-Dogar |
| 5,297,963 A | | 3/1994 | Dafatry |
| 5,492,471 A | * | 2/1996 | Singer ........................... 433/172 |
| 5,513,989 A | | 5/1996 | Crisio |
| 5,564,925 A | | 10/1996 | Shampanier |
| 5,591,029 A | | 1/1997 | Zuest |
| 5,810,592 A | | 9/1998 | Daftary |
| 6,068,479 A | | 5/2000 | Kwan |

(Continued)

OTHER PUBLICATIONS

International Search Report and Written Opinion of PCT/US2011/022737 mailed on Mar. 23, 2011, 10 pages.

(Continued)

*Primary Examiner* — Heidi M Eide
(74) *Attorney, Agent, or Firm* — Kilpatrick Townsend & Stockton LLP

(57) ABSTRACT

A dental implant system includes a base member that is adapted to be embedded within a patient's jawbone at a treatment site. The base member has a generally flat top side defining an outer periphery, a bottom side, and a central opening. At least one recess is included in the top side for receiving an alignment pin. The system further includes an implant screw that has a head and a threaded end. The threaded end is adapted to pass through the central opening of the base member and into the patient's jawbone. Also, the head is adapted to be seated within the central opening of the base member after the threaded end is screwed into the patient's jawbone. The implant screw further includes a threaded opening in the head.

19 Claims, 27 Drawing Sheets

(56) References Cited

U.S. PATENT DOCUMENTS

| | | | |
|---|---|---|---|
| 6,120,292 | A | 9/2000 | Buser et al. |
| 6,168,436 | B1 | 1/2001 | O'Brien |
| 6,250,922 | B1 | 6/2001 | Bassett et al. |
| 6,287,117 | B1 | 9/2001 | Niznick |
| 6,436,103 | B1 * | 8/2002 | Suddaby .................. 606/96 |
| 6,454,569 | B1 | 9/2002 | Hollander et al. |
| 6,537,069 | B1 | 3/2003 | Simmons, Jr. |
| 6,843,653 | B2 | 1/2005 | Carlton |
| 6,863,529 | B2 | 3/2005 | Strong et al. |
| 7,056,117 | B2 | 6/2006 | Simmons, Jr. |
| 7,097,451 | B2 | 8/2006 | Tang |
| 7,101,177 | B2 | 9/2006 | Lin |
| 7,806,685 | B1 | 10/2010 | Grant |
| 8,231,388 | B2 | 7/2012 | Grant |
| 8,287,278 | B2 | 10/2012 | Grant |
| 2002/0076673 | A1 | 6/2002 | Wagner et al. |
| 2003/0180686 | A1 | 9/2003 | Simmons, Jr. |
| 2004/0265781 | A1 | 12/2004 | Coatoam |
| 2006/0014120 | A1 | 1/2006 | Sapian |
| 2006/0093988 | A1 * | 5/2006 | Swaelens et al. .......... 433/76 |
| 2008/0118892 | A1 | 5/2008 | Adams |
| 2008/0124675 | A1 | 5/2008 | Adams |
| 2009/0226857 | A1 | 9/2009 | Grant |
| 2009/0258329 | A1 | 10/2009 | Adams |
| 2010/0112522 | A1 | 5/2010 | Kwon |
| 2010/0159419 | A1 | 6/2010 | Grant |
| 2010/0266987 | A1 | 10/2010 | Ford |
| 2010/0330534 | A1 | 12/2010 | Hyun |
| 2011/0118742 | A1 | 5/2011 | Hulliger et al. |
| 2012/0196250 | A1 | 8/2012 | Grant |

OTHER PUBLICATIONS

Stud. (n.d.), Dictionary.com Unabridged, retrieved Apr. 20, 2011, from Dictionary.com website: http://dictionary.reference.com/browse/stud.

Teeth. (n.d.), Dictionary.com Unabridged, retrieved Apr. 20, 2011, from Dictionary.com website: http://dictionary.reference.com/browse/teeth.

Plate. (n.d.), Dictionary.com Unabridged, retrieved Dec. 1, 2010 from Dictionary.com website: http://dictionary.reference.com/browse/plate, 12 pages.

Examiner's Report of Canada Patent Applcation No. 2732001 mailed on Nov. 2, 2012, 3 pages.

* cited by examiner

DENTAL PLATFORM ASSEMBLY AND METHODS

CROSS-REFERENCES TO RELATED APPLICATIONS

This application is a continuation-in-part application of copending U.S. application Ser. No. 12/694,911 filed Jan. 27, 2010 which is a continuation-in-part of copending U.S. application Ser. No. 12/243,676, filed Oct. 1, 2008 which is a continuation-in-part application of co-pending U.S. application Ser. No. 12/074,524 filed on Mar. 4, 2008. The complete disclosures of each of these applications are herein incorporated by reference.

BACKGROUND OF THE INVENTION

Implants are popular means of replacing a lost tooth. Due to their relatively low maintenance and durability people often prefer implants to bridges. Nevertheless, there is a largely undocumented body of complaints voiced to front line dentists about implants, by their patients. These complaints generally are about food impacting and accumulating around and beneath the crown portion of the implant in the enlarged periodontal gap between the implant and the adjacent teeth.

BRIEF SUMMARY OF THE INVENTION

The invention describes various dental implant systems as well as methods for securing such systems within a patient's jaw. In one embodiment, such a method includes the step of removing a portion of the patient's gum at a treatment site sufficient to expose the patient's jawbone. A portion of the patient's jawbone at the treatment site is also removed to form a recess. This recess preferably has a shape and size similar to a base member that will subsequently be placed into the recess. This base member has a generally flat top side defined by an outer perimeter and a tapered central opening. The base member is positioned in the recess, typically with the top side being flush with a top surface of the jawbone. A drill bit is placed through the central opening and a hole is drilled in the jawbone. An implant screw is inserted through the central opening. This implant screw has a head with a tapered section and a threaded end. The implant screw is turned to secure the threaded end within the hole in the jawbone and to seat the head of the implant screw within the tapered opening of the base member.

In some cases drill bits of increasing size may be inserted into the central opening to progressively expand the size of the hole in the jawbone. In one particular aspect, the base member is generally rectangular in geometry as is the recess in the jawbone.

With the base member secured, an abutment is placed onto the top surface of the base member. To help prevent rotation of the abutment relative to the base member, the top side of the base member may include at least one recess and a locating pin that is placed in the recess. The locating pin is inserted into a corresponding recess on the abutment when placing the abutment onto the base member.

In one aspect, the implant screw includes a threaded hole. In this way, a capture screw may be inserted through a central opening of the abutment and into the threaded hole to secure the abutment to the base member. Further, the implant screw may be seated into the jawbone using a torque wrench using a force of at least about 35 Ncm.

The abutment may include a locating sleeve extending from the central opening of the abutment. The locating sleeve may be placed into the central opening of the base member to help position the abutment on the base member.

Prior to placement of the abutment, a healing cover may be placed onto the base member and the patient's gun sutured over the healing cover. The healing cover in one aspect extends to the outer perimeter of the base member. After the site as healed, the healing cover is accessed and removed from the base member. A tissue contouring cap may then be placed onto the base member using a screw that extends into the implant screw. This helps to form the surgical site area and prepare it for receiving the crown. After the tissue has properly formed, the healing cover is removed and the abutment is secured to the base using a capture screw that extends through the abutment and into the implant screw. Further, a crown is attached to the abutment.

In one particular aspect, the base member has a generally flat bottom side, and the central opening tapers inward from the top surface to the bottom surface with a constant taper. Also, the base member has an outer periphery that tapers with a straight taper inward from the top surface to the bottom surface such that the top surface is greater in surface area than the bottom surface. Further, the outer periphery of the base member may be roughened.

The invention further provides a dental implant system that comprises a base member that is adapted to be embedded within a patient's jawbone at a treatment site. The base member has a generally flat top side defining an outer periphery, a bottom side, and a central opening. At least one recess is included in the top side for receiving an alignment pin. The system further includes an implant screw that comprises a head and a threaded end. The threaded end is adapted to pass through the central opening of the base member and into the patient's jawbone. Also, the head is adapted to be seated within the central opening of the base member after the threaded end is screwed into the patient's jawbone. The implant screw further includes a threaded opening in the head.

The system may further include an abutment that is configured to be placed onto the top side of the base member so that a crown may be placed on the abutment. The abutment comprises a flat bottom surface that is configured to be positioned adjacent the top side of the base member. The bottom surface of the abutment has an outer perimeter that generally matches the outer periphery of the base member. The bottom surface defines at least one recess that is aligned with the recess in the base member when the abutment is placed onto the base member. The abutment further includes a shaped upper surface that is adapted to receive a crown and a through hole extending longitudinally through the abutment.

In some cases, a locating sleeve may extend from the through hole of the abutment and into the head of the implant screw. Also, an alignment pin may be placed within the recess of the base member and the abutment. Further, a capture screw may be inserted through the through hole of the abutment, through the locating sleeve and into the threaded opening in the head of the implant screw.

In one aspect, the abutment and the base member each include a second set of recesses. These recesses are aligned with each other when the abutment is placed onto the base member. Another alignment pin is placed within the second set of recesses. In a further aspect, the sleeve is cylindrical in geometry, and the capture screw has an upper end with a smooth outer surface that is configured to fit within the sleeve.

In one particular aspect, the central opening is tapered, and the implant screw has a tapered head section to seat within the tapered central opening. Also, the base member may be generally rectangular in geometry. Further, the outer periphery of the base member may taper inward from the top surface to the bottom surface such that the top surface is greater in surface area than the bottom surface. The outer periphery of the base member may be roughened.

In yet a further embodiment, the invention provides a platform for securing a dental crown to a patient's jawbone. The platform comprises a base member that is adapted to be embedded within a patient's jawbone at a treatment site. The base member has a generally flat top side, a generally flat bottom side, an outer periphery, and a central opening that tapers inward with a constant taper from the top surface to the bottom surface and is configured to receive an implant screw. The top side further includes a pair of recesses that are adapted to receive alignment pins that are configured to be received within corresponding recesses of an abutment to ensure non-rotatable alignment of the abutment with the base member.

In one particular embodiment, the invention further provides an exemplary method for securing a dental implant (or implant screw) to a patient's jawbone. According to the method, a portion of the patient's gum is removed sufficient to expose the patient's jawbone. This may be done after the patient's tooth or other dental work has been removed. Also, a portion of the patient's jawbone is removed. The depth of bone removal may be in the range from about 1 mm to about 4 mm. A base member is positioned at the treatment site such that it is embedded within the patient's jawbone wherein the bone has been removed. The base member may have a generally flat top side defined by an outer perimeter, a tapered central opening and at least one screw hole that is positioned between the central opening and the outer perimeter. A small securing screw is placed through the screw hole and rotated until it is screwed into the patient's jawbone and a head of the securing screw is at least flush with the top side of the base member. In this way, the base member is embedded within and securely fastened to the patient's jawbone. This base member will subsequently serve as a stable platform for a prosthesis. An implant screw is placed through the central opening of the base member. The implant screw has a head with a tapered section and a threaded end. The implant screw is turned to secure the threaded end within the jawbone and to seat the head of the implant screw within the tapered opening of the base member. Once the implant screw is secured to the jawbone and appropriate healing has occurred, a prosthesis, such as a crown, may be coupled to the implant screw.

In one aspect, the base member includes two screw holes that are positioned between the outer periphery and the central opening. As one example, the base member may be generally rectangular in geometry, with the two screw holes being located in corners of the base member. This serves to further secure the base member to the patient's jawbone. Also, when the base member is rectangular, the surgeon may also surgically remove a rectangular section of the jawbone so that the base member will fit within the resulting depression in the jawbone.

In another aspect, the top side of the base member may be embedded within the jawbone such that it is generally flush with the top surface of the patient's jawbone. In a further aspect, the top side may further include at least one matable feature that is configured to mate with a corresponding feature on a crown to ensure non-rotatable alignment of the crown with the base member. The implant screw may further include a threaded hole and the crown may include a bolt so that the bolt may be screwed into the threaded hole.

In yet another aspect, the base member may have a generally flat bottom side, and the central opening may taper inward from the top surface to the bottom surface with a constant taper. Further, the base member may have an outer periphery that tapers with a straight taper inward from the top surface to the bottom surface such that the top surface is greater in surface area than the bottom surface.

In some cases, the outer periphery of the base member may be roughened to increase the surface area of the base member. This in turn serves to enhance bone growth to the base member.

In another embodiment, the invention provides a dental implant system that comprises a base member that is adapted to be embedded within a patient's jawbone at a treatment site. The base member has a generally flat top side defining an outer periphery, a bottom side, a central opening, and at least one screw hole positioned between the central opening and the outer periphery. The system also includes an implant screw that comprises a head and a threaded end that is adapted to pass through the central opening of the base member and into the patient's jawbone. The head of the implant screw is adapted to be seated within the central opening of the base member after the threaded end is screwed into the patient's jawbone. The system further includes a securing screw that is smaller in size than the implant screw and has a head and a threaded end. The threaded end of the securing screw passes through the screw hole of the base member and into the patient's jawbone. In this way, the securing screw may be used to help further secure the base member to the patient's jawbone. In turn, this helps to stabilize the implant screw and the prosthesis that will be coupled to the implant screw.

In one aspect, the central opening is tapered and has a beveled edge. Also, the implant screw has a tapered head section to seat within the tapered central opening. This particular configuration is also useful in preventing microleakage between the base member and the implant screw.

In another aspect, the base member is generally rectangular in geometry, and the securing hole is located in a corner of the base member. In one particularly useful arrangement, the base member has two securing holes for use with two securing screws. The securing holes are located in opposing corners of the base member. Also, the securing holes may have a tapered section and the heads of the securing screws may have a tapered section. Further, the securing screws may each have a pointed end and a diameter of about 1.5 mm.

In a further aspect, the base member includes a plurality of retention grooves that are located on the outer periphery. Also, the outer periphery of the base member may tapers inward from the top surface to the bottom surface such that the top surface is greater in surface area than the bottom surface. With this arrangement, the taper may begin below retention grooves. Additionally, the outer periphery of the base member is roughened to facilitate bone growth.

The system may be used with various prosthesis. For example, a crown may be mounted to the head of the implant screw. In some cases, the top side of the base member may includes at least one matable feature, and the crown may also include a corresponding matable feature that mates with the feature on the base member to non-rotationally secure the crown to the base member. The implant screw may include a threaded hole and the crown may include a bolt so that the bolt may be screwed into the threaded hole.

In yet another embodiment, the invention provides a platform for securing a dental crown to a patient's jawbone. The platform comprises a base member that is adapted to be embedded within a patient's jawbone at a treatment site. The base member has a generally flat top side, a generally flat bottom side, an outer periphery, a central opening and a screw hole positioned between the central opening and the outer periphery. The central opening tapers inward with a constant taper from the top surface to the bottom surface and is configured to receive an implant screw. The top side may further include at least one matable feature that is configured to mate with a corresponding feature on a crown to ensure non-rotatable alignment of the crown with the base member.

In one aspect, the outer periphery may include a plurality of retention grooves, and the outer periphery may taper with a straight taper inward from the retention grooves to the bottom surface such that the top surface is greater in surface area than the bottom surface. In another aspect, the base member may be generally rectangular in geometry, and the securing hole is located in a corner of the base member. Two or more securing holes and securing screws may also be used.

Figure 1:
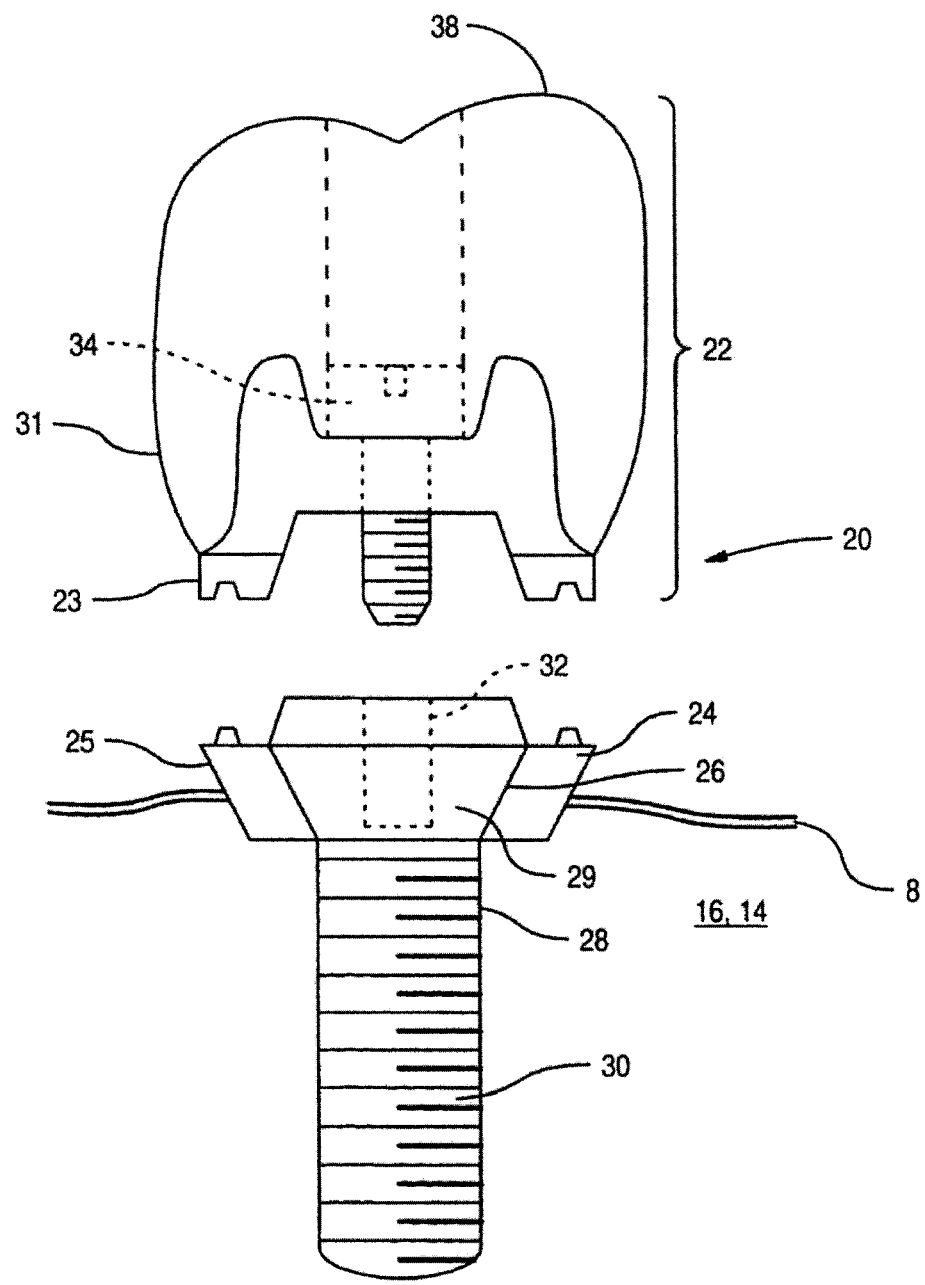
FIG. 1 is a side elevation diagram of an implant having an enlarged base seated directly on the jaw.

The following is a discussion and description of specific embodiments of this invention, such being made with reference to the drawings, wherein the same reference numerals are used to indicate the same or similar parts and/or structure. It should be noted that such discussion and description is not meant to unduly limit the scope of the invention.

DETAILED DESCRIPTION OF THE INVENTION

Restoring the edentulous space of missing first and second molars and bicuspids can be problematic. This is because these teeth are typically square or rectangular in geometry. Typical dental procedures restore this space using round dental implants. When the crown is placed onto the implant, there are excessive voids between the crown and adjacent teeth. These spaces serve as food traps and will eventually lead to tooth decay of the adjacent teeth. This problem generally arises because the implant is round yet is trying to fill a generally square or rectangular space.

One important feature of the invention is a way to provide a platform that generally fills this edentulous space so that when a square or rectangular crown is placed onto the implant there is minimal space between the crown and the adjacent teeth. The platforms of the invention are generally square or rectangular and are positioned about the implant to provide a convenient surface to attach the crown. In some cases, part of the patient's jawbone may be removed so that the platform may be countersunk within the patient's jawbone. In this way, when the crown is placed onto the platform not only will it be generally aligned with the adjacent teeth but the jawbone will tend to grow about the platform to provide a stable surface to support the crown.

A wide variety of platforms may be used in connection with most commercially available implants. Typically, the outer periphery of the platform will be generally rectangular or square and will have a central opening through which the implant may be inserted. The top surface of the platform is typically flat in geometry. However, it may include one or more detents or other features to mate with a corresponding feature on the crown and/or abutment so as to prevent rotation of the crown relative to the platform. Also, the platform may have one or more holes to permit small surgical screws to be inserted through the platform and into the jawbone so that the platform may be further secured to the patient's jawbone. These holes may be countersunk so that the surgical screws are generally flush with the top surface of the platform. The outer and bottom surfaces of the platform may have various grooves or roughened surfaces to facilitate bone healing and bone grown to the platform.

Once the platform is securely in place it essentially converts the round implant into a square or rectangular implant so as the match the outer geometry of the crown. In this way, voids or spaces between adjacent teeth are minimized to prevent decay and tooth loss that may otherwise result from the placement of the implant and crown.

FIG. 1 is a side elevation diagram of an improved tooth implant assembly 20 having a base 24 for seating on jaw 16. In one embodiment, tooth implant assembly 20 includes base plate 24, a base attachment fastener 28 (also referred to as an implant screw or simply an implant), a crown attachment fastener 34, a crown supporting mechanism 36 (FIG. 2), and a tooth crown 38.

Generally, the tooth implant assembly 20 comprises: i) a crown portion 22 having a lower portion 23 adapted for seating and connection; ii) base 24 having an upper portion adapted to matably receive the crown portion 22, a lower portion adapted to seat directly on (or be embedded within)

the bone 14 of one of the jaws 16, the base 24 having an upright, or central, opening 26 therethrough; and, iii) a base attachment fastener 28 having a head 29 adapted to be seated o and around upright opening 26, and a threaded end portion, or shaft, 30 for screwable reception in the jaw 16 to thereby anchor the base 24 thereon. The base 24 of the implant 20 is enlarged to better distribute load on the jaw 16 and thereby additionally allow said crown portion 22 to have more upright peripheral sidewalls 31, so that embrasures, or periodontal gaps, 12 (FIGS. 3-7) between the bottom portion of the crown portion and adjacent teeth 10 (FIGS. 3-7) are thereby substantially reduced, and so that both food impaction and collection therein is also substantially reduced. In one embodiment, the base 24 is generally rectangular and non-rotatable.

Base attachment fastener 28 is adapted for insertion into and engagement with central opening 26 in base plate 24. In one embodiment, base attachment fastener 28 is a bone screw.

Head 29 of base attachment fastener 28 has a central bore 32 formed longitudinally in the body of fastener 28. In one embodiment, central bore 32 of base attachment fastener 28 extends into threaded shaft 30. In one embodiment, head 29 of base attachment fastener 28 is a countersink head adapted to fit countersunk central opening 26.

Within this specification "jaw" 16 is intended and defined to include either the upper jaw or the lower jaw. Similarly, within this specification "bone" 14 is intended and defined to include either the maxilla or the mandible.

If base 24 is sized generally similarly to the bottom portion of a removed tooth (not shown) then the periodontal gaps 12 on opposite sides of the implanted crown portion 22 will not be enlarged. The base 24 may be further enlarged to maximally minimize the periodontal gaps 12 between the implant 20 and adjacent teeth 10.

In one embodiment of the invention, the base 24 has a sloping peripheral sidewall 25 and the bottom side portion is smaller in area than the top side portion. The bottom side portion of the base 24 may be embedded within the bone 14 of the jaw 16. This may be done by removing a piece of the patient's jawbone prior to adhering base 24 to the jawbone. Alternatively, if bone 14 strength is an issue, the bottom side portion of the base 24 may be generally fitted to the vertical curvature of the bone 14 of the jaw 16.

In another embodiment of the invention, the peripheral sidewall 25 of the base 24 is coated or roughened to facilitate gum 8 adhesion thereto. In one embodiment, the upper portion of the base attachment screw 28 comprises an internally threaded hole, or central bore, 32 for reception of a crown attachment bolt 34. It is also contemplated that the top portion of the base 24 and the bottom side portion of the crown 22 are matingly configured to ensure proper and non-rotatable alignment of the crown portion 22 on the base 24.

Figure 2:
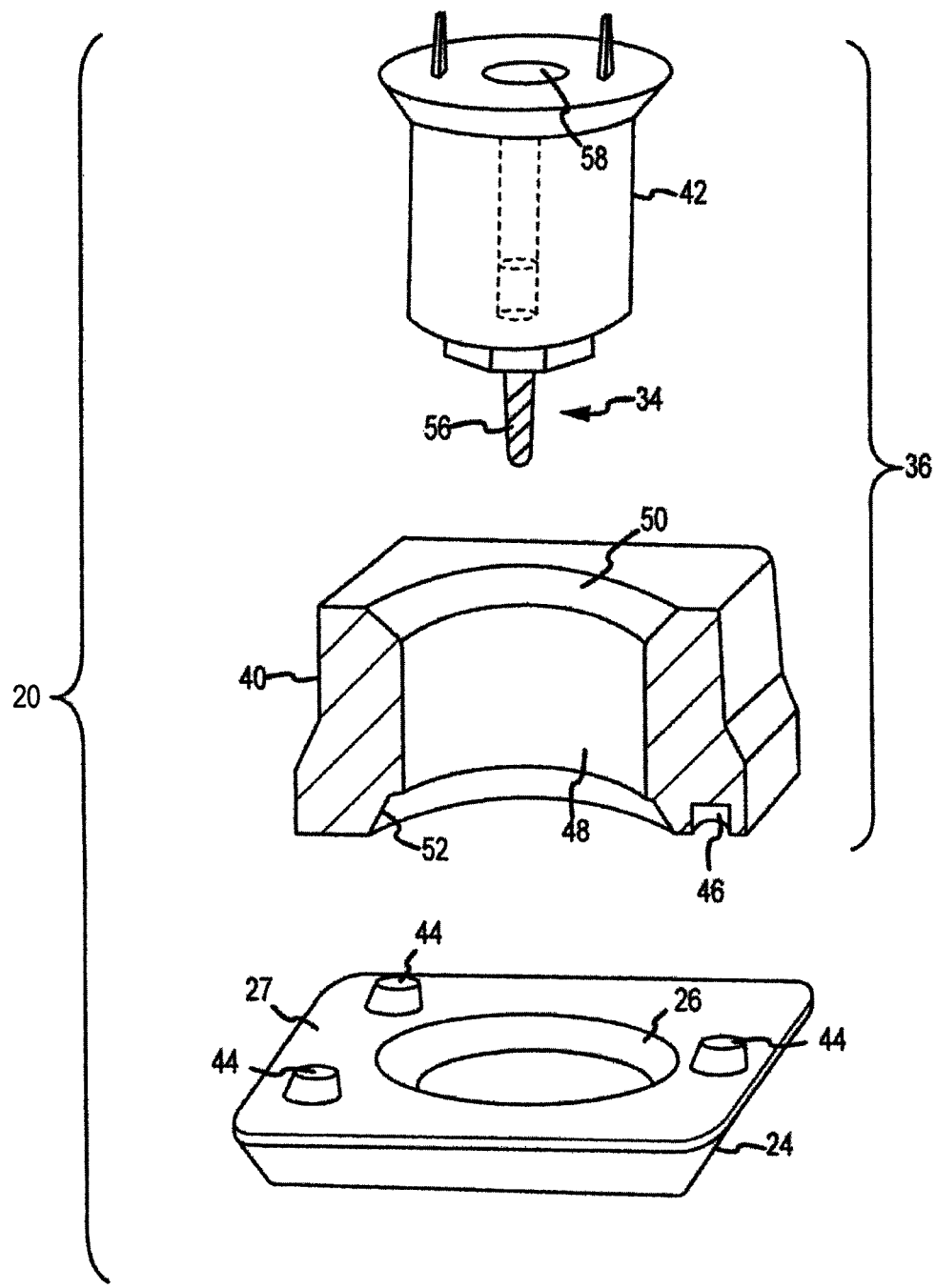
FIG. 2 is an exploded view of the base plate and crown supporting means of the implant.

FIG. 2 is a more detailed illustration of the base plate 24 and crown support mechanism 36 of implant 20. Tooth crown 38 is supported by and attached to crown supporting means 36. Together tooth crown 38, crown supporting mechanism 36, and crown attachment screw 34 embody crown portion 22.

Base plate 24 has central opening 26 and coronal surface 27. The terms "coronal" and "apical" are used in this specification to describe the side of a structure closest to the crown apex (root), respectively, of a tooth.

In one embodiment, central opening 26 of base plate 24 is countersunk. Central opening 26 may be beveled at any angle, even a concave angle, or it may be straight with no bevel. In one embodiment, coronal surface 27 is a flat surface. In one embodiment, coronal surface 27 of base plate 24 includes teeth means 44 for engagement, such as a plurality of upstanding studs 44.

Crown supporting mechanism 36 carries crown attachment fastener 34. Crown supporting mechanism 36 is disposed on coronal surface 27 of base plate 24. In one embodiment, crown support mechanism 36 includes recessions 46 for engaging detents 44 (also referred to as upstanding studs) of coronal surface 27. Of course, it will be appreciated that the recessions and detents may be on opposite parts or intermixed between the two parts.

In one embodiment, crown support mechanism 36 includes a collar 40 (also referred to as an abutment collar) and a cylindrical insert 42. Collar 40 is shown partially cut away in FIG. 2. Collar 40 includes longitudinal opening 48 with coronal 50 and apical 52 edges. Collar 40 is disposed on coronal surface 27 of base plate 24.

Cylindrical insert 42 is disposed within collar 40 and supported by coronal edge 50 of collar 40. Cylindrical insert 42 has a longitudinal channel 58 formed therein for carrying crown attachment fastener 34.

Crown attachment fastener 34 is adapted for threaded engagement with central bore 32 of base attachment fastener 28. In one embodiment, crown attachment fastener 34 has a threaded shaft 56 adapted for threaded engagement with central bore 32.

It will also be appreciated that any one of a variety of commercially available prosthesis may be coupled to implant 30 as is known in the art. As such, the invention is not limited to a specific crown attachment fastener, collar abutment, or prosthesis. Rather, embodiments of the invention provide a way to stabilize the implant screw and prosthesis using a stabile base or platform that is secured to the bone.

Generally, the method of implanting a tooth implant or prosthesis 20 in a jaw 16 comprises the following steps that do not necessarily need to proceed in order. The method utilizes a tooth implant 20, such as the one generally described above. A pilot hole 6 is drilled in the jawbone and is sized to accommodate the internal diameter of the base attachment screw 28. The hole 6 is laterally centered in the jaw 16 between adjacent teeth 10 in a open space left by a removed tooth (not shown). Sufficient gum 8 is removed to allow the base 24 to seat directly on the bone 14 of the jaw 16. Optionally, a portion of the jawbone may be removed so that base 24 may sit within the jawbone and be flush with the top surface. Once the treatment site is surgically prepared, the threaded end portion 30 of the base attachment screw 28 is positioned through the upright opening 26 in the base 24 and screw 28 is screwed into the bone 14 of the jaw 16 thereby attaching the base 24 to the jaw 16. As described hereinafter, base 24 may first be secured to the patient's jawbone by using one or more smaller screws that extend through the base and into the jawbone. These may be located, for example, between the central opening of base 24 and its outer perimeter. With base 24 secured and screw 28 in place, the surgeon may position, fit and maintain the removed gum 8 peripherally around the base 24 that is now attached to the jaw 16. A crown portion 22 may be molded and may have a bottom portion sized to fit on the base 24 and a top portion sized appropriately to fill the open space between the adjacent teeth 10. The molded crown portion 22 may be attached to the base 24 that is anchored on the jaw 16. The base 24 of the implant 20 is enlarged to better distribute load on the jaw 16, so that periodontal gaps 12 between the bottom portion of the crown portion 22 and adjacent teeth 10 are thereby reduced, and so that both food impaction and collection therein is minimal. This most general method may be detailed with the apparatus limitations specified above under the most general description of the tooth implant 20.

FIGS. 3-7 illustrate an embodiment for installing a tooth implant in a jaw 16 having bone 15 and gum 8. Although the steps represented in FIGS. 3-7 are presented in a specific order, the technology presented herein can be performed in any variation of this order. Furthermore, additional steps may be executed between the steps illustrated in FIGS. 3-7.

Figure 3:
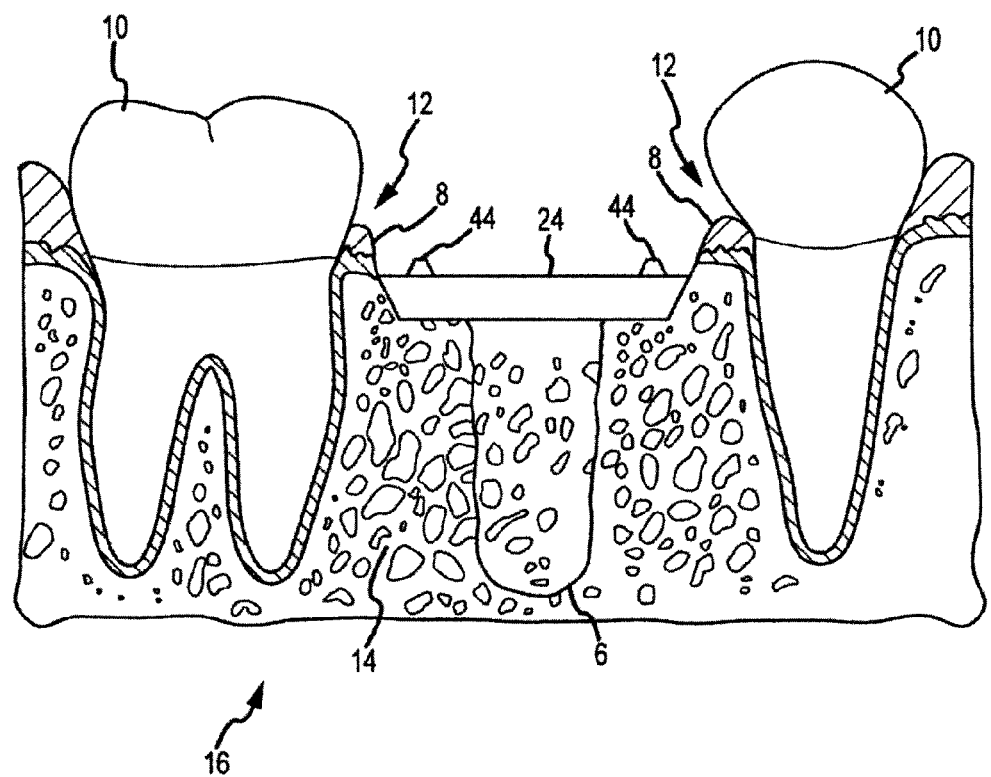
FIGS. 3-7 illustrate an embodiment of steps in a method for installing the tooth implant of FIG. 1.
Figure 4:
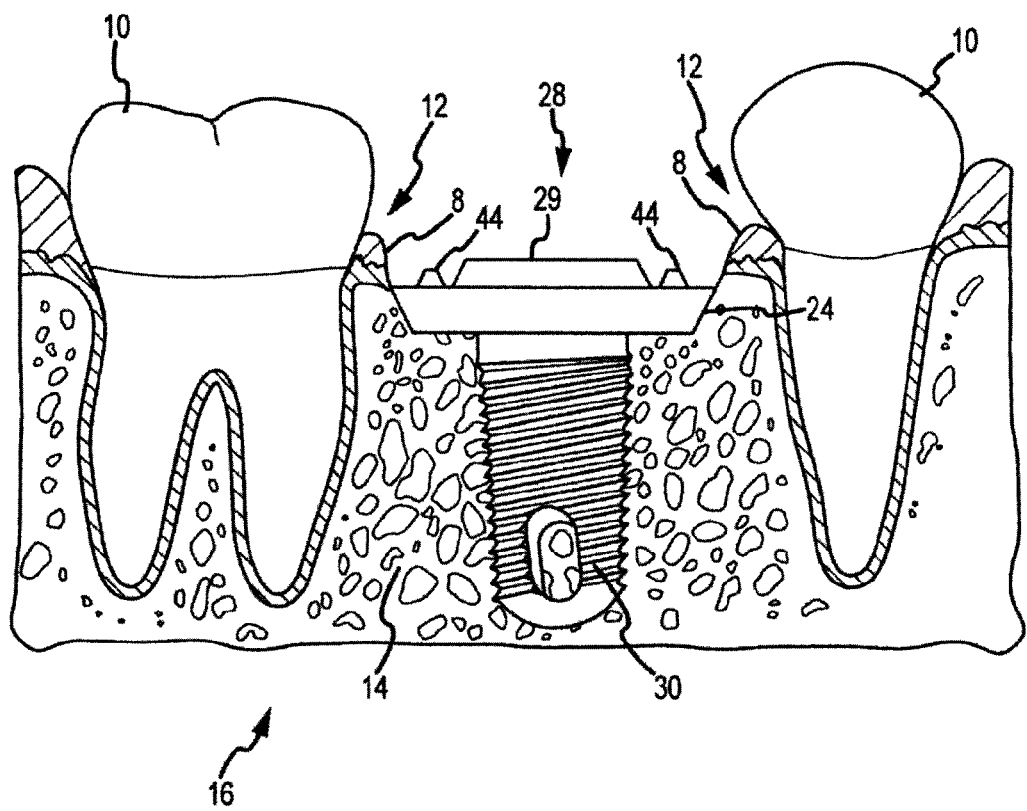
Figure 5:
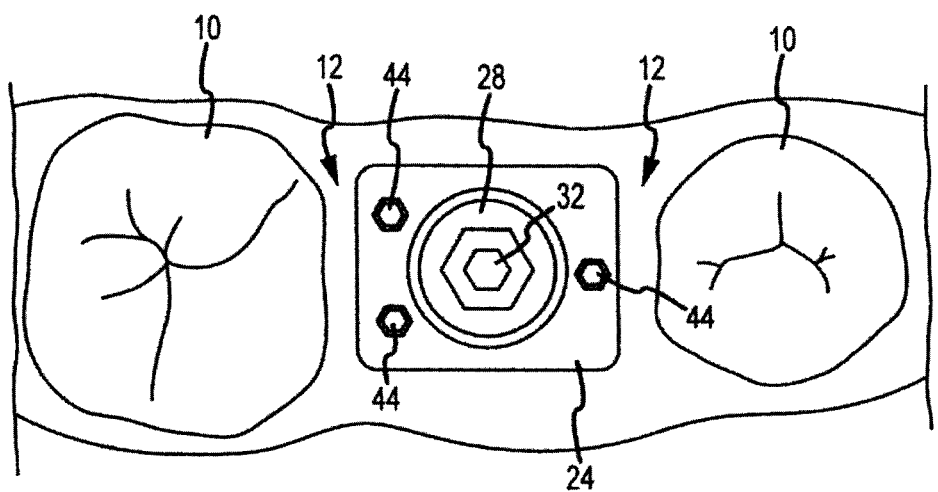

FIGS. 3 and 4 are side elevations of base plate 24 being fastened to jaw 16. FIG. 5 is a top elevation of the step shown in FIG. 4. In one embodiment, fastening base plate 24 to jaw 16 includes drilling a pilot hole 6, removing gum 8 and or bone 14 from jaw 16, and positioning threaded shaft 30 of base attachment screw 28 through central opening 26. Typically, enough bone may be removed so that the top surface of base plate 24 is flush with the top of bone 14. Although not shown, base plate 24 may include one or more through holes through which small surgical screws may be used to secure base plate 24 to bone 14. This may be done prior to or after inserting attachment screw 28.

Pilot hole 6 is typically sized to accommodate the internal diameter of base attachment screw 28. Pilot hole 6 is laterally centered in jaw 16. Also, sufficient gum 8 is removed from jaw 16 to allow base plate 24 of implant 20 to seat directly on bone 14 of jaw 16 (in cases where no bone is removed). Threaded shaft 30 of base attachment screw 28 is positioning through central opening 26 in base 24 of implant 20. Screw 28 is screwed into bone 14 of jaw 16 thereby attaching base plate 24 to jaw 16.

Figure 6:
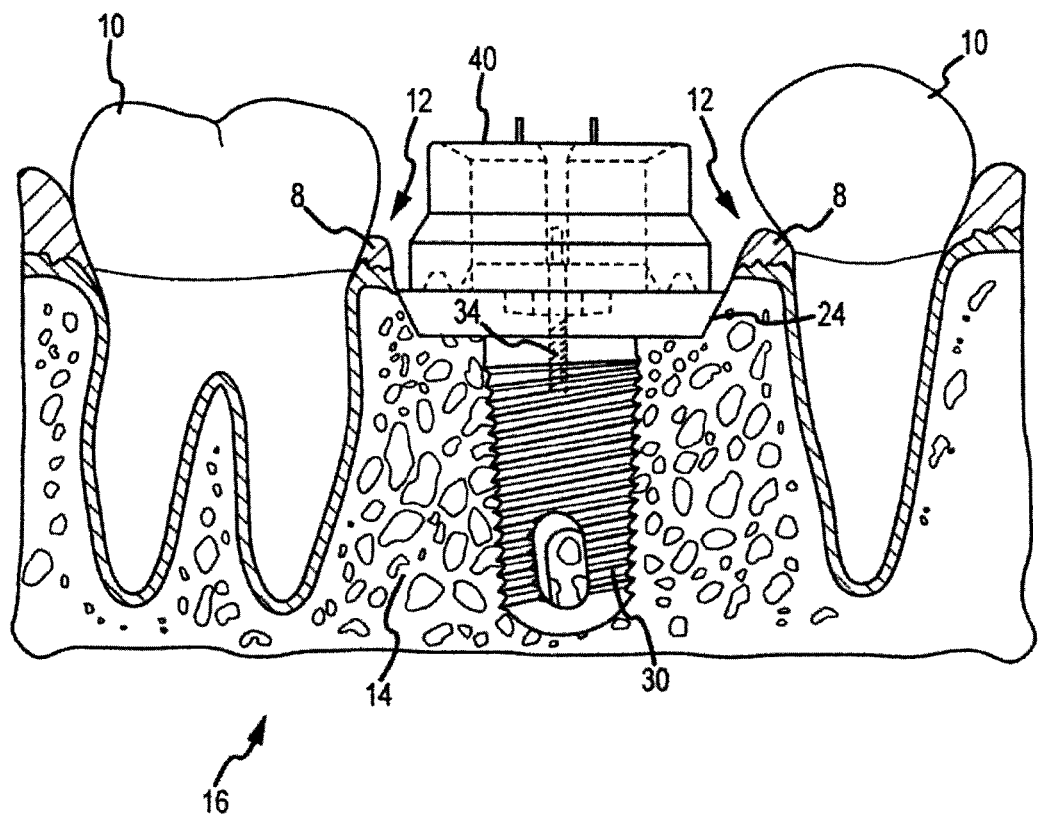
Figure 7:
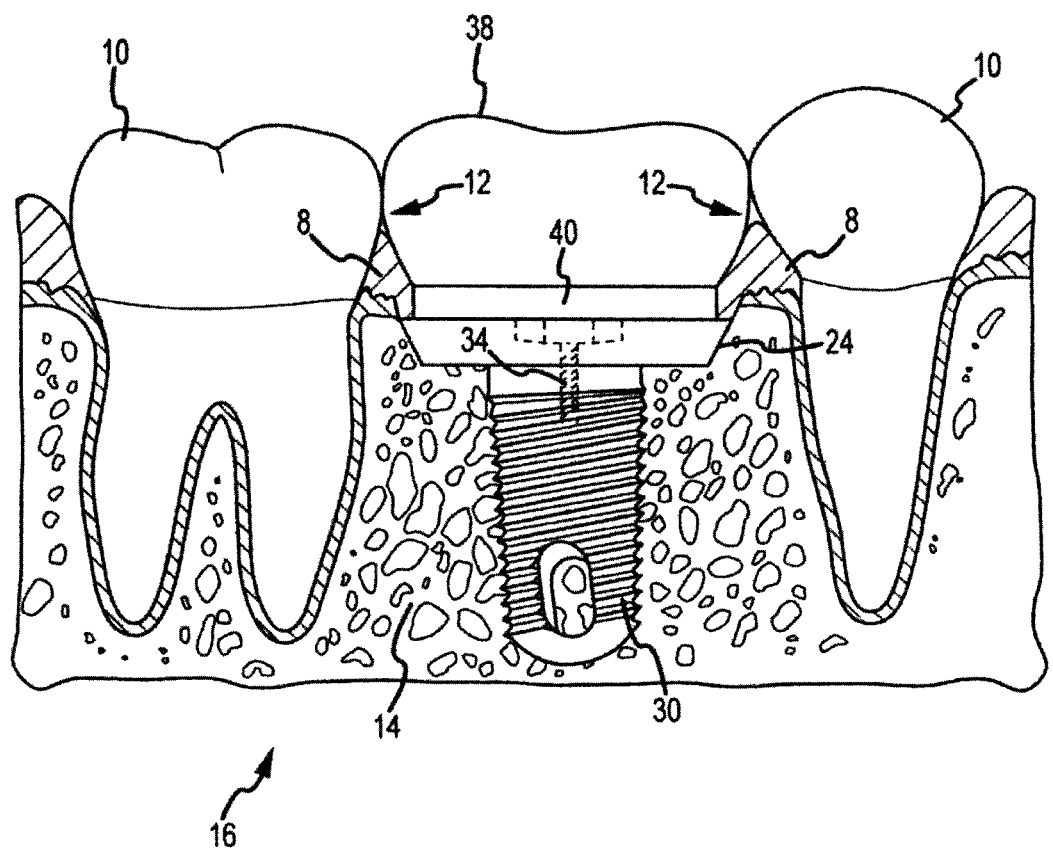

FIG. 6 is a side elevation showing collar 40 being affixed to base plate 24. Longitudinal opening 48 is provided in collar 40. Collar 40 is disposed on coronal surface 27 of base plate 24. Crown attachment fastener 34 is inserted through collar 40. Cylindrical insert 42 is disposed within collar 40. FIG. 7 is a side elevation showing tooth crown 38 being attaching to collar 40.

Figure 8:
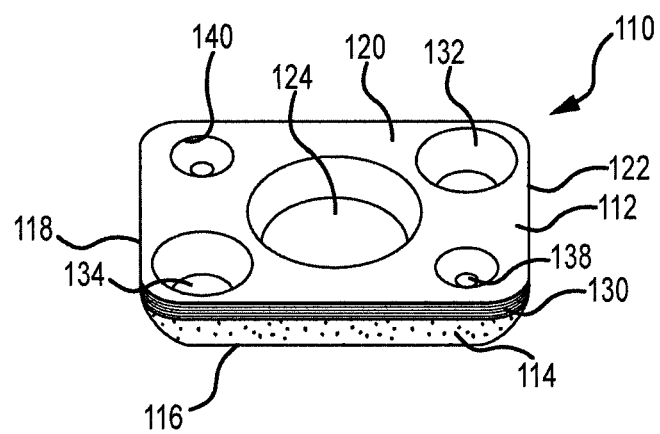
FIG. 8 is a top perspective view of one embodiment of a platform or base according to the invention.
Figure 9:
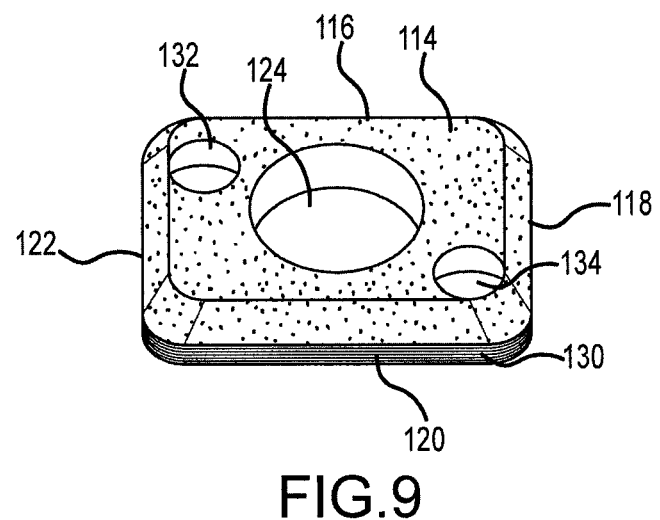
FIG. 9 is a bottom perspective view of the base of FIG. 8.

Referring now to FIGS. 8 and 9, one exemplary embodiment of a base 110 will be described. Base 110 is constructed of a stable material, such as polished titanium, ceramics, zirconia, or the like. Base 110 has a generally flat top surface 112 and a bottom surface 114. Base 110 also has four outer edges or sides 116, 118, 120 and 122. Formed in the center of base 110 is a central opening 124 through which an implant is inserted. Central opening 124 is beveled or tapered so that it generally matches the shape of the head of the implant. This tapering also assists to provide microleakage between base 110 and the implant.

Base 110 is generally square or rectangular in geometry and may have rounded corners. Typically, the length of sides 116 and 120 will be in the range of about 7 mm to about 12 mm, and more typically from about 8 mm to about 12 mm. The length of the opposing sides 118 and 122 may be in the range from about 5 mm to about 10 mm, and more particularly from about 6 mm to about 9 mm. The thickness of base 110 between top 112 and bottom 114 will typically be about 1 mm to about 4 mm, and more typically from about 2 mm to about 3 mm. Also, sides 116, 118, 120 and 122 may be angled from top 112 to bottom 114. Such angling of the sides is particularly useful for directing chewing force into the platform and bone and transferring it to the center implant to evenly disperse the load. Also, the sides and bottom 114 may be roughened to facilitate bone integration. For example, a pressure blasted aluminum oxide micro etching process may be used. Other processes include acid etching or other techniques to increase the surface area of the sides and the bottom. Also, grooves 130 may be placed on the sides of base 110 to also increase surface area and facilitate bone integration.

Also extending through base 110 are a pair of screw holes 132 and 134. These screw holes are also beveled or tapered to permit small surgical screws to be inserted through these holes and be flush with the top surface 112. These small screws extend into the patient's jawbone and serve to secure base 110 to the patient's jawbone. As shown, base 110 includes two screw holes which are located at opposing corners of the base. However, it will be appreciated that different numbers of screw holes could be used. For example, base 110 could be constructed with only a single screw hole. Alternatively, it could employ three screw holes, with two being in adjacent corners and one being on the opposite side. As another option, four screw holes could be employed, with the four holes being located in each of the corners. In still a further options, base 110 may not include any such screw holes, relying on bone adhesion to secure base 110 within the patient's jawbone.

Base 110 also includes two detents or dimples 138 and 140 in top surface 112. These dimples are designed to receive mating features on the abutment to prevent rotational movement of the abutment relative to base 110 once the abutment is secured to the implant. Although shown with dimples, it will be appreciated that other types of non-rotational features may be used. For example, bumps or ridges could be included on top surface 112 to mate with detents or dimples on the abutment. Also, any number of such non-rotational features could be employed.

Figure 10:
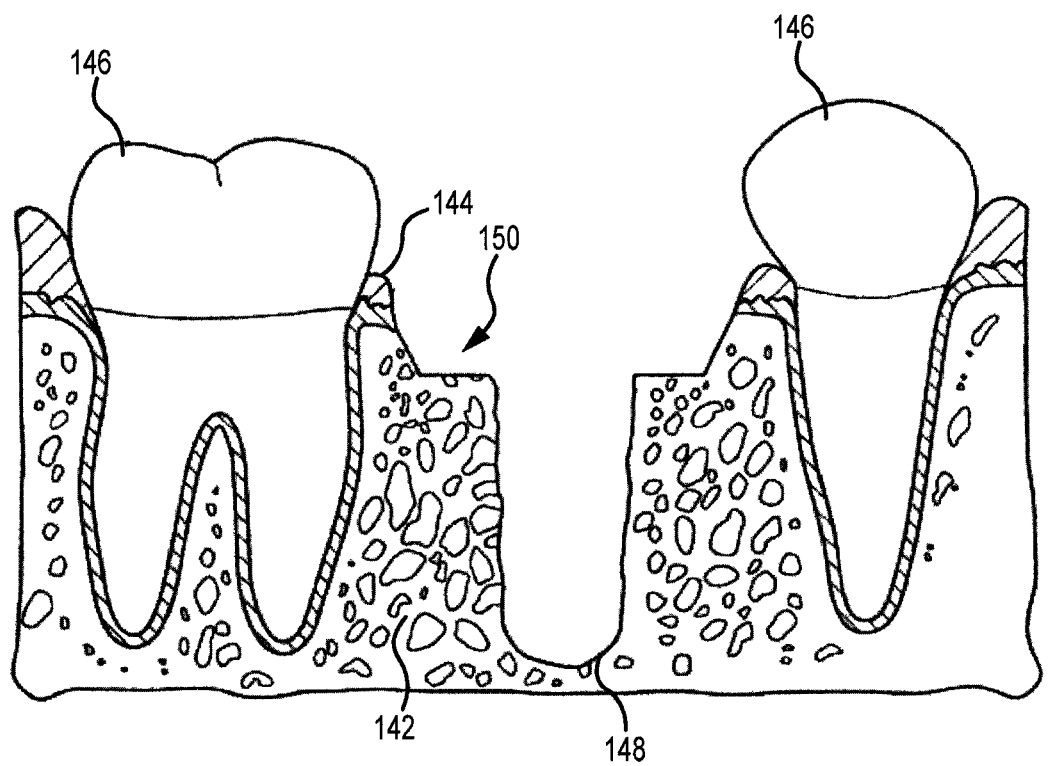
FIG. 10 illustrates a cross-sectional side view of a patient's jawbone that has been drilled to receive an implant and in which a rectangular portion has been surgically removed in order to receive a base according to the invention.
Figure 11:
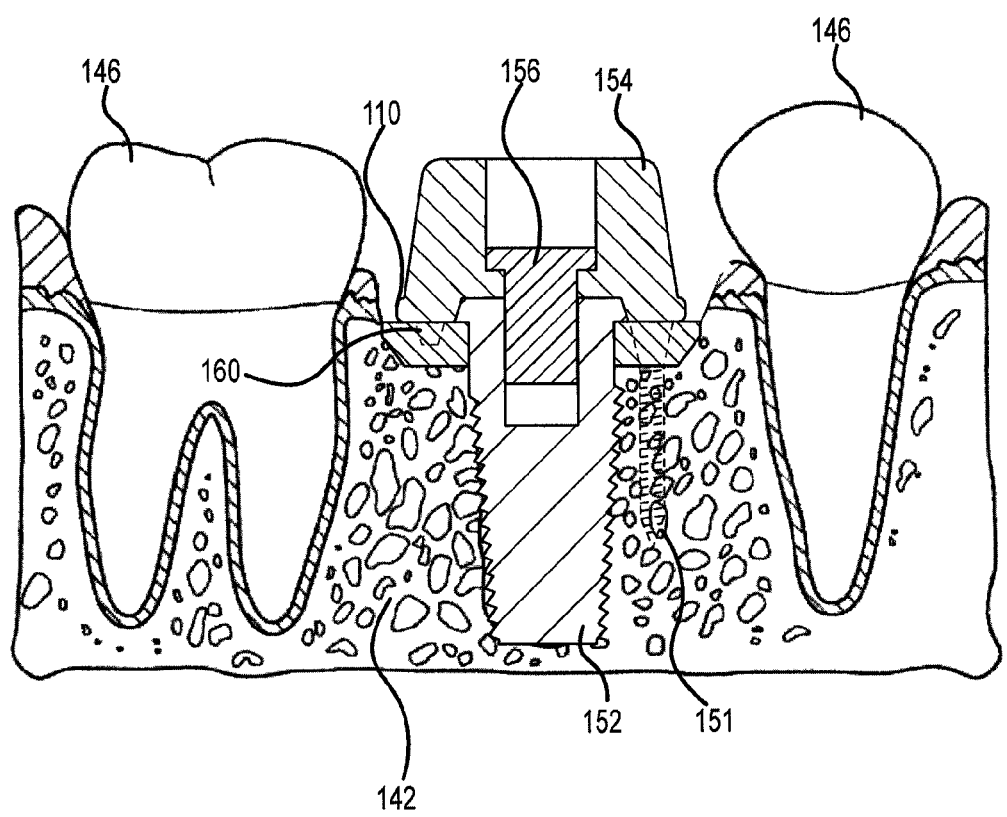
FIG. 11 illustrates an implant that has been inserted into the jawbone of FIG. 10 with a corresponding base and abutment.
Figure 12:
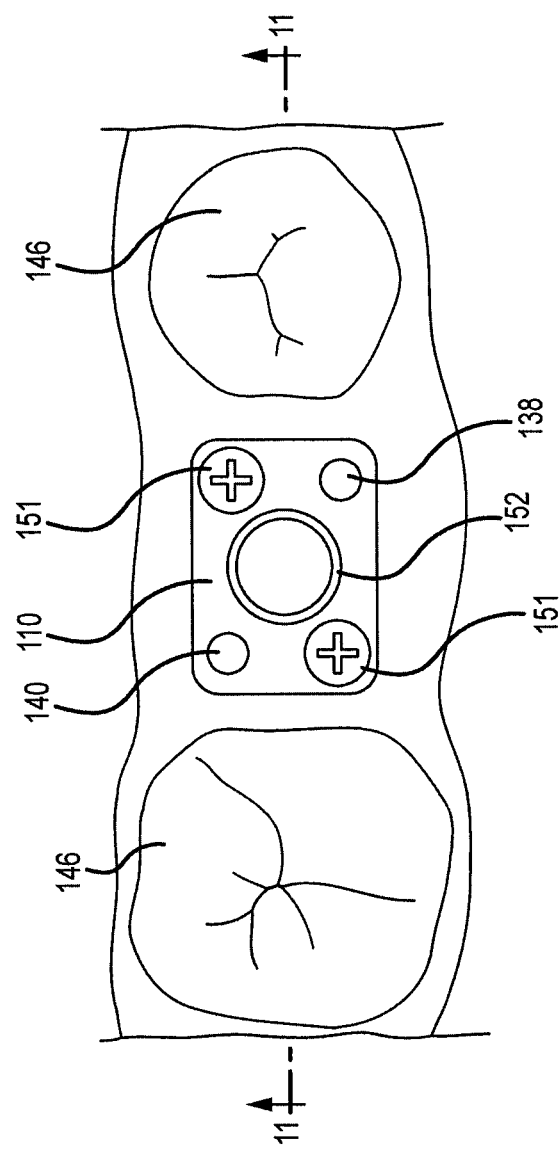
FIG. 12 is a top view of the base and implant of FIG. 11 prior to attachment of the abutment.

FIG. 10 illustrates a cross-sectional view of a patient's jawbone prior to placement of base 110 or an implant. In FIG. 10, the patient's jawbone is illustrated by reference numeral 142 and the tissue or gum line above the patient's jawbone is illustrate by reference numeral 144. As shown, one tooth has been removed leaving a space or void between adjacent teeth 146. Prior to placement of an implant or a base, an appropriate hole 148 is drilled and a generally square or rectangular recess 150 is cut into the patient's jawbone. As illustrated in FIG. 11, base 110 has been secured within recess 150. The sides 116, 118, 120 and 122 generally match with the outer sides or walls of recess 150 while bottom 114 rests upon the removed portion of the jawbone. To secure base 110 in place, screws 151 have been inserted through screw holes 132 and 134 (see FIG. 8) and into the jawbone. Screws 151 will typically have a length in the range from about 5 mm to about 11 mm, and more typically from about 7 mm to about 9 mm. In this way, base 110 is secured to the patient's jawbone 142. Top surface 112 is generally flush with the top of the patient's jawbone so that it essentially functions as part of the patient's jawbone. A more detailed view of screws 151 that secure base 110 to the patient's jawbone is illustrated in FIG. 12.

Once base 110 is securely in place, an implant 152 is screwed into the opening 148 until the head of the implant is seated within central opening 124. At this point, a screw or healing cap may be inserted into the top end of implant 152 and remain in place for several weeks until bone has properly healed and adhered to base 110. The healing cap may then be removed so that an abutment 154 (see FIG. 11) may be secured to base 110. For example, a hex 156 may be screwed through a central opening of abutment 154 and into implant 152. Also, bumps 160 on the undersurface of implant 154 mate with detents 138 and 140 on base 110 to prevent rotational movement of abutment 154 relative to base 110. Once abutment 154 is securely in place a prosthesis, such as a crown, is secured to abutment 154. The outer shape of abutment 154 is generally square or rectangular in geometry and therefore matches the outer shape of base 110. In this way, voids or gaps between the crown that is placed on abutment 154 and the adjacent teeth 146 is minimized. Typically, the outer edges of abutment 154 will come within about 1 mm to about 4 mm of side walls 116, 118, 120 and 122. This provides sufficient space for the resulting crown that will be placed on top of abutment 154.

Figure 13:
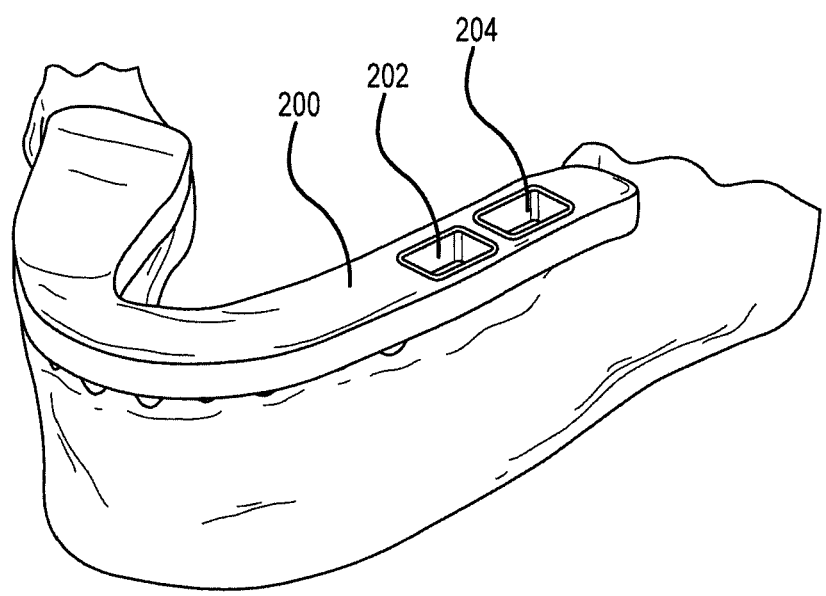
FIG. 13 is a perspective view of a template that may be employed when surgically removing portions of the patient's jawbone according to the invention.

FIG. 13 is a perspective view of a template 200 that may be used when surgically producing the sites needed for placement of an implant and base as described in previous embodiments. Template 200 is molded so that it fits over the patient's teeth. Also, template 200 has two through holes 202 and 204 that serve as guides when removing the patient's jawbone at a treatment site. Although shown with two through holes, it will be appreciated that any number may be used depending on the number of implant sites. Through holes 202 and 204 are specifically aligned with where the patient's removed teeth were previously located. In this way, when a surgical device, such as a hand-held router, is directed through the through holes 202 and 204, it produces a rectangular recess in the patient's jawbone.

Figure 14:
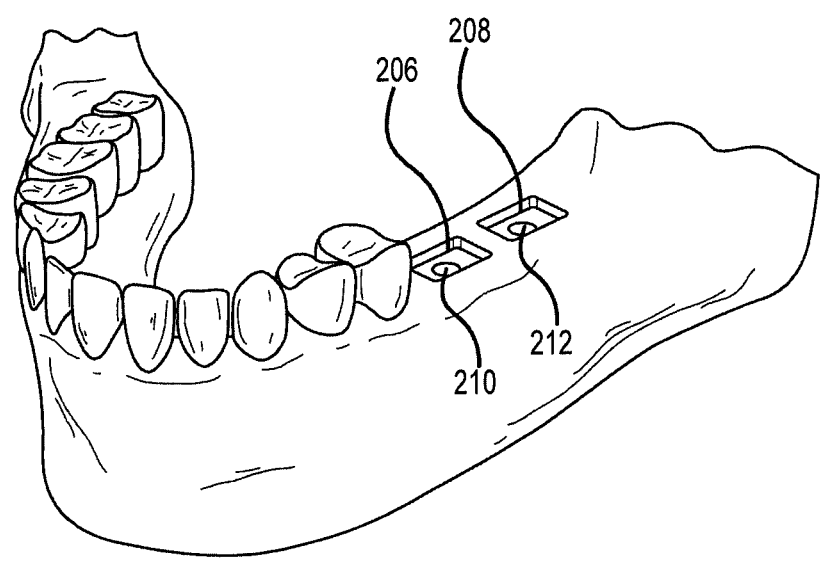
FIG. 14 illustrates the surgical recesses formed within the patient's jawbone using the template of FIG. 13.

FIG. 14 illustrates the recesses 206 and 208 that are formed within the patient's jawbone when using template 200 of FIG. 13. Also shown are two holes 210 and 212 that have been drilled to receive the implant. Above holes 210 and 212 are the rectangular recesses 206 and 208 in the jawbone which are sized to receive bases or platforms as described herein.

Figure 15:
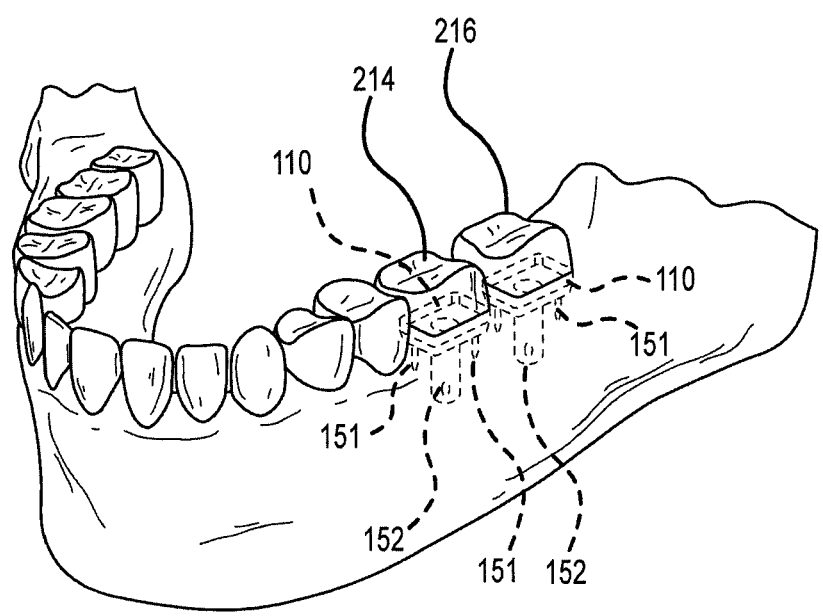
FIG. 15 illustrates crowns that have been restored to the surgical sites of FIG. 14 according to the invention.
Figure 16:
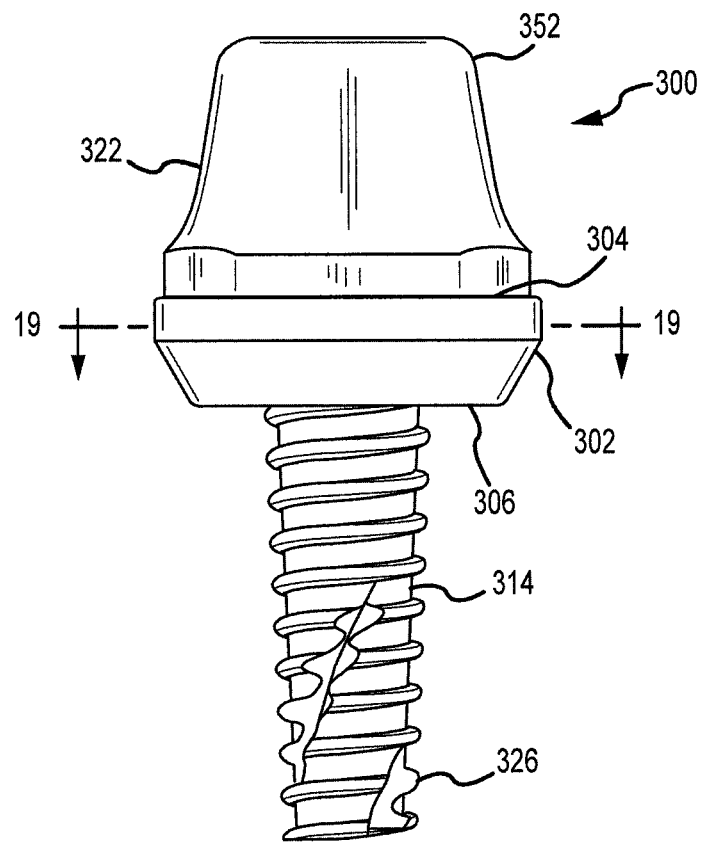
FIG. 16 illustrates a side view of one particular embodiment of a dental implant system according to the invention.
Figure 17:
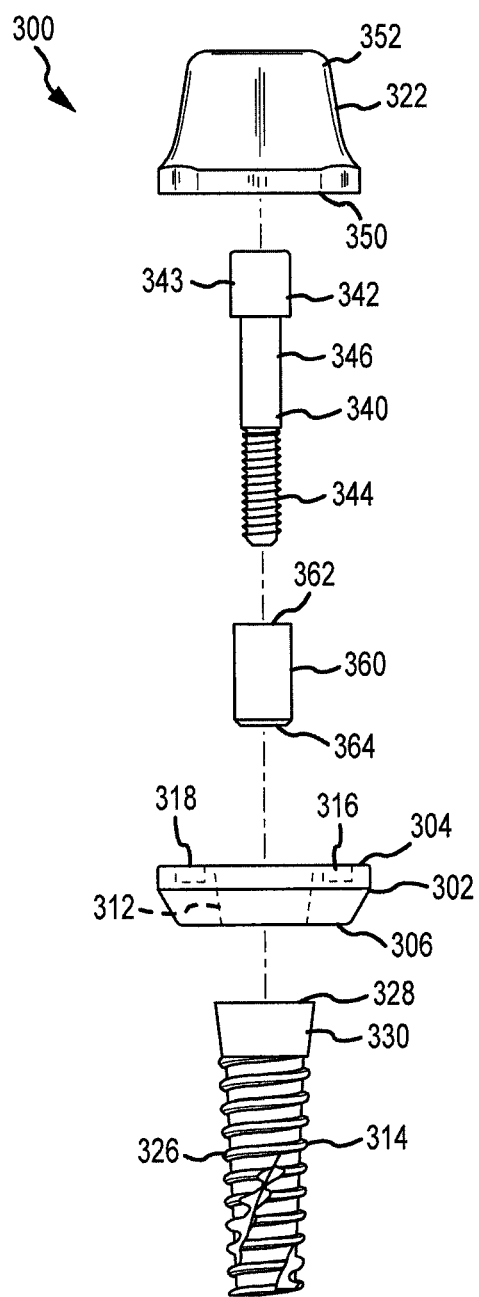
FIG. 17 is an exploded view of the dental implant system of FIG. 16.
Figure 18:
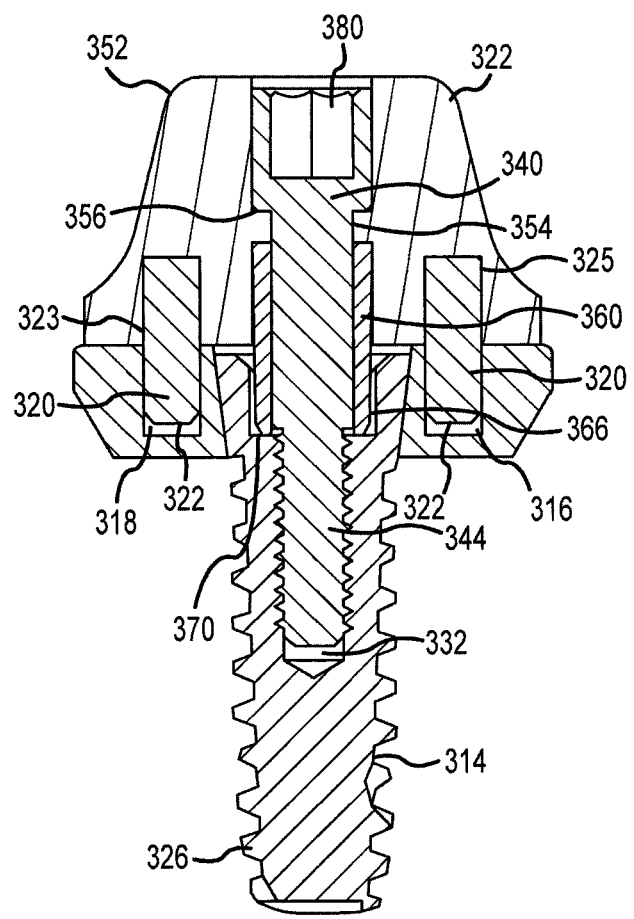
FIG. 18 is a cross sectional view of the dental implant system of FIG. 19 taken along lines 18-18.

FIG. 15 illustrates in phantom line the implants 152, bases 110 and surgical screws 151 previously described in connection with FIG. 11. Also positioned on top of each base is a crown 214 and 216. Not shown in phantom line for convenience of illustration are the abutments that sit between the crowns and the base. As shown, the space between each crown and/or adjacent tooth is minimized by the nature of the rectangular bases. In this way, the amount of food or other material that may be potentially trapped between two adjacent teeth and/or crowns is minimized.

FIGS. 16-19 illustrate another embodiment of a dental implant system 300. System 300 includes a base member 302, sometimes also referred to as a platform. Base member 302 has a flat top side 304, a bottom side 306 and an outer periphery 308. Similar to other embodiments described herein, outer periphery 308 is a generally rectangular in geometry with rounded corners. The outer periphery may be sized to generally match the size of the crown that is to be placed onto base member 302. For instance, in the example illustrated hereinafter, base member 302 may have a length (in a direction aligned with the jawbone) that is the range from about 7 mm to about 12 mm, and more particularly about 9 mm and a width (generally perpendicular to the length of the jawbone) in the range from about 5 mm to about 10 mm, and more particularly about 7 mm. The depth of base member 302 as measured from top side 304 to bottom side 306 may be in the range from about 1 mm to about 4 mm, and more particularly about 2.5 mm. Other shapes and sizes are possible, particularly depending on the size and the shape of the tooth for which it is replacing. Merely by way of example, base member 302 may be circular, oval, square, octagonal, hexagonal, or even custom shaped to the shape of a tooth. All or only a portion of the sides of base member 302 may be tapered so that top side 304 is greater in surface area than bottom side 306. In the example illustrated, approximately the top third of base member 302 has sides that are perpendicular to top side 304. The bottom two-thirds of the side walls taper inward at an angle. The reason for tapering of the side walls is to facilitate placement of base member 302 into a recessed region of the patient's jawbone. By tapering the side walls, a practitioner can more easily place the base member 302 into the recess which may have a relatively tight fit.

Materials that may be used to construct base member 302 include titanium, ceramics, zirconia, and the like. As with other embodiments described herein, the walls and bottom side 306 of base member 302 may be roughened, coated or treated with a surface treatment to increase the surface area of the base member in order to enhance bone growth or osseointegration.

Figure 19:
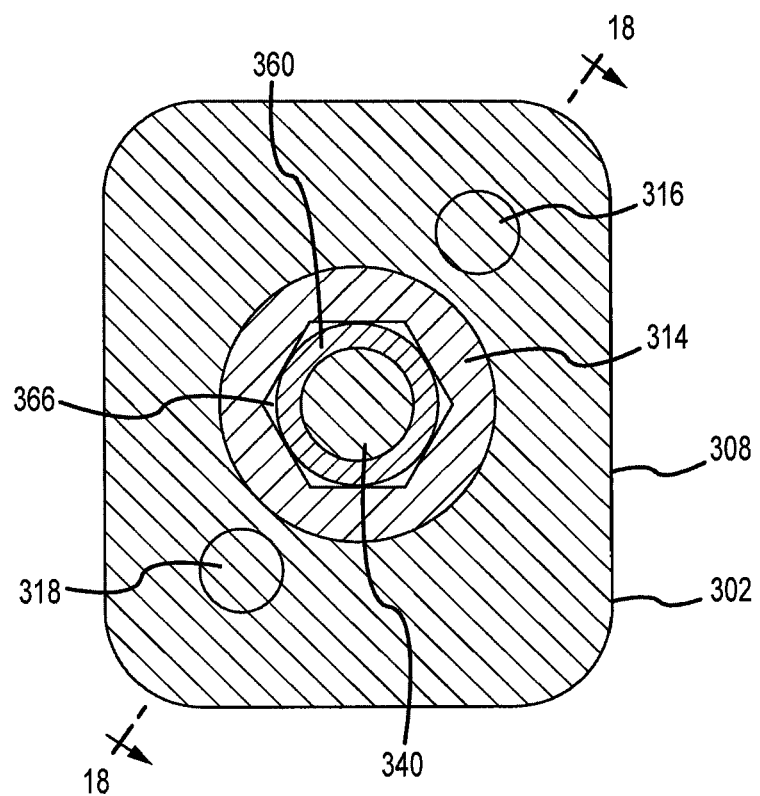
FIG. 19 is a cross sectional view of the dental implant system of FIG. 16 taken along lines 19-19.

Base member 302 further includes a central opening 312 that extends completely through the base member 302. Central opening 312 tapers from top side 304 to bottom side 306 to permit a cold weld to be formed between an implant screw 314 as described hereinafter. Base member 302 further includes a pair of recesses 316 and 318. As best illustrated in FIG. 19, recesses 316 and 318 are positioned on the diagonal of top side 304 and are cylindrical in geometry. Recesses 316 and 318 are each designed to receive an alignment pin 320. These alignment pins are used to align an abutment 322 on top side 304 of base member 302. Pins 320 are also used to prevent abutment 322 from rotating relative to base member 302. Pins 320 are press fit into recess 316 and 318, typically by a force applied by human fingers. Pins 320 are cylindrical in geometry and may be constructed of materials similar to those used for base member 302. Also, a bottom end 322 of pins 320 may be chamfered to facilitate introduction into recesses 316 and 318. Similar to other embodiments, other alignment or anti-rotation mechanisms could also be used, including detents or other interlocking elements.

Although shown with two recesses and alignment pins, it will be appreciated that other numbers may be included, such as a single pin, or more than two pins. Further, the recesses and pins may have other sizes, shapes and locations on base member 302. For example, the pins could be square and located midway between two opposite sides of base member 302.

Implant screw 314 includes a threaded end 326, a head 328 and a tapered head section 330. Extending through head 328 is a threaded opening 332 (see FIG. 18). Threaded end 326 is configured to be screwed into the patient's jawbone after passing through central opening 321 of base member 302. Typically, implant screw 314 will have a length that extends well below base member 302 so as to be fully implanted in the bone. Implant screw 314 may be constructed of a biocompatible material, such as titanium. Tapered section 330 has a smooth outer surface that directly contacts the surface of central opening 312. As torque is applied to implant screw 314, a cold weld is formed between tapered section 330 and base member 302 to prevent bacteria from travelling down into the jawbone.

Threaded opening 332 is configured to receive a capture screw 340 that secures abutment 322 to base member 302. Capture screw 340 has an upper end 342 with a head 343 and a threaded lower end 344. Also, upper end 342 includes a smooth shank 346.

Abutment 322 includes a bottom surface 350 and an upper surface 352. A through hole 354 extends through abutment 322 and includes a shoulder 356 (see FIG. 18) that is configured to engage with head 343 of capture screw 340 to securely seat implant 352 against top side 304 of base member 302. Also, recess 323 and 325 are used to receive alignment pins 320.

The lower portion of through hole 354 is configured to receive a cylindrical locating sleeve 360. The inner surface of locating sleeve 360 is configured to be placed about shank 346. Locating sleeve 360 includes a top end 362 and a chamfered bottom end 364. Locating sleeve 360 is configured to be placed into head 328 of implant screw 314, preferably by a press fit. To do so, head 328 includes a space 366 located above threaded opening 332. Locating sleeve 360 not only serves to assist in aligning abutment 322 with base member 302, but also serves to mechanically secure these two parts together. In some cases, locating sleeve 360 may be omitted, making this part optional. Space 366 is also used to receive a torquing instrument, such as an Allen's wrench, when tightening implant screw 214. As best shown in FIG. 19, space 366 can be hexagonal in shape, although other geometries may be used. Locating sleeve 360 is used to facilitate placement of abutment 322 onto base member 302 and also the placement of capture screw 340 into threaded opening 332. In use, locating sleeve 360 is pressed through central opening 312 and into space 366 of implant screw 314, with the chamfer on bottom end 364 facilitating its placement. Locating sleeve 360 is inserted into space 366 until resting on a shoulder 370. Abutment 322 is then placed onto base member 302, with locating sleeve 360 extending into through hole 354, preferably with a press fit. Capture screw 340 may then be inserted through through hole 354 where it passes through locating sleeve 360 and into opening 332.

Capture screw 340 may also include a hexagonal opening 380 in head 343 that permits a wrench to apply a torque to capture screw 340. By turning capture screw 340 into implant screw 314, bottom surface 350 of implant 322 is forced against top side 304 of base member 302. Both top tide 304 and bottom surface 350 are manufactured to be sufficiently smooth so that no more than about 20 microns of space is between them when screw 340 is tightened. In this way, a tight seal is provided between abutment 322 and base member 302.

Figure 20:
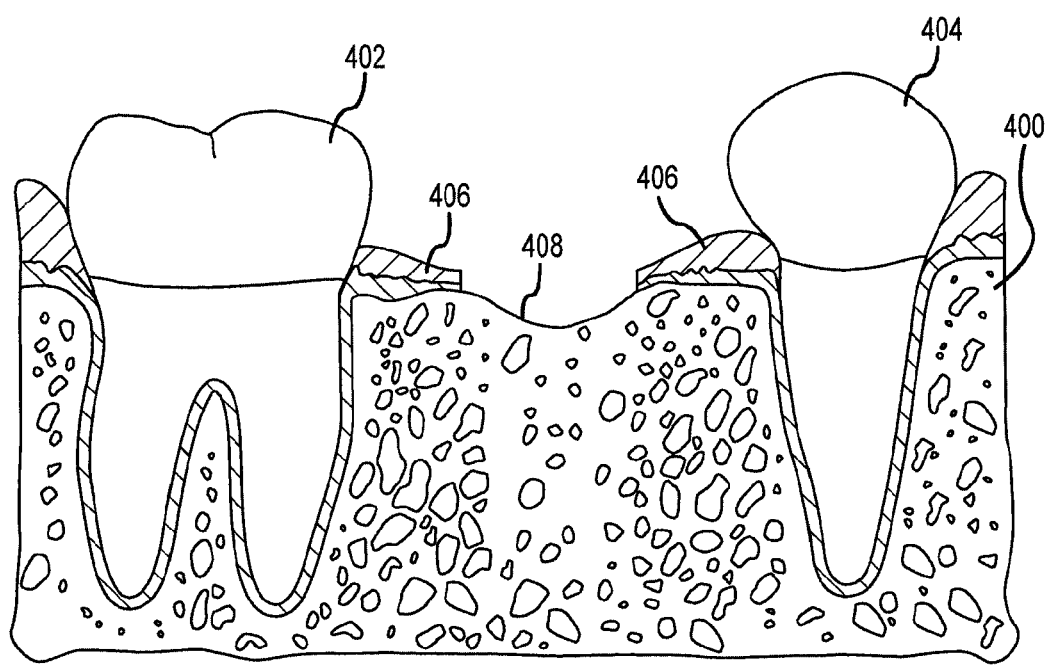
FIG. 20 illustrates a portion of a patient's jawbone where a tooth has been removed.

Referring now to FIGS. 20-28 one exemplary method for placing the dental implant system of FIGS. 16-19 will be described. FIG. 20 illustrates a cross section of a patient's jawbone 400 where a tooth has been removed, leaving an opening between teeth 402 and 404. Initially, tissue 406 is dissected, by laying open a flap of tissue, to expose bone 400 at a surgical site 408.

Figure 21:
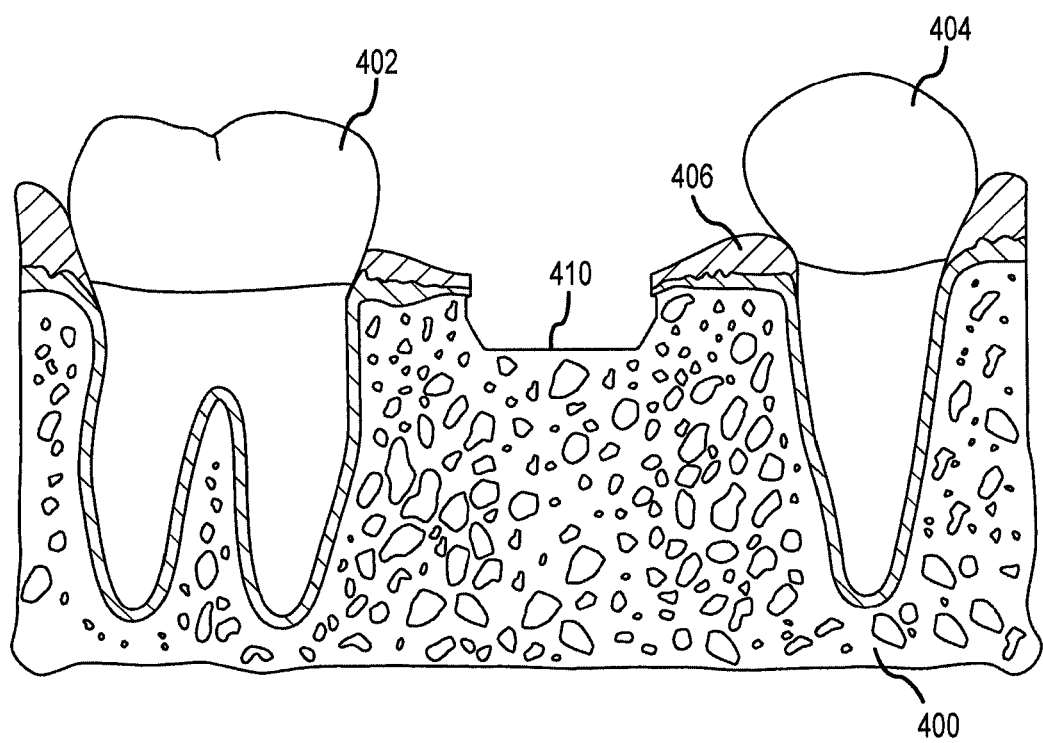
FIG. 21 illustrates the portion of the patient's jawbone of FIG. 20 with a portion of the jawbone removed to form a recess.
Figure 22:
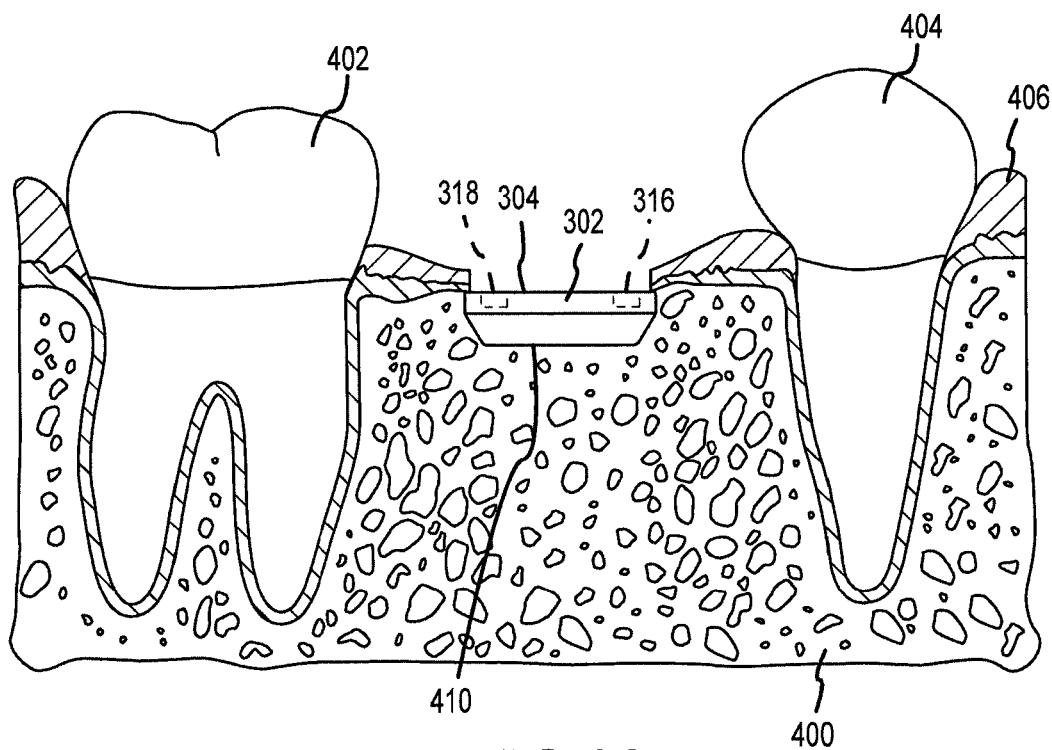
FIG. 22 illustrates the jawbone of FIG. 21 with a base member or platform inserted into the recess.

In FIG. 21, a section of bone 400 is removed to form a recess 410. Bone 400 may be removed in a variety of ways, including by use of a router, a drill, or the like. Recess 410 preferably is formed to have the same size, shape and depth of the base member so that minimal bone growth will be required in order to fully secure the base member to bone 400. Base member 302 is then placed within recess 410 such that top side 304 is generally flush with the top of bone 400, just below the gum line. In this way, as base member 302 becomes integrated within bone 400 it takes the same overall shape as the bone before surgery. With proper bone integration, additional securing screws may not be needed to hold base member 302 within recess 410, thereby providing a smoother surface between top side 304 and bottom surface 350 of abutment 322.

Figure 23:
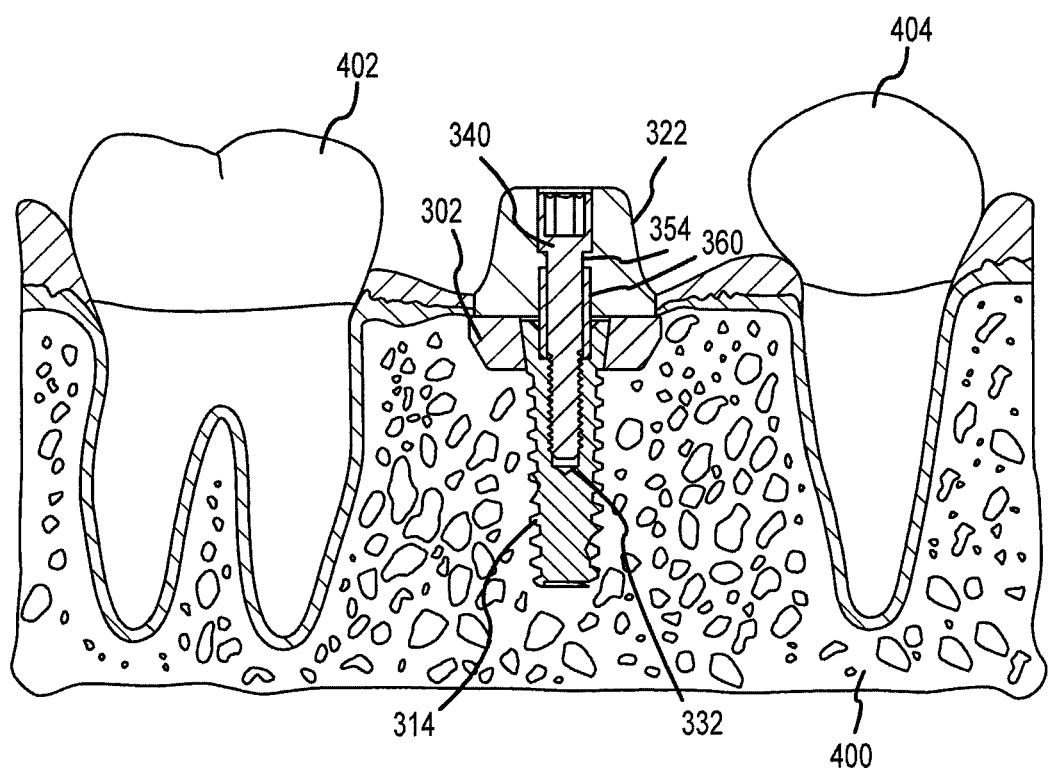
FIG. 23 illustrates a drill passing through the base member that is used to create a hole in the patient's jawbone.
Figure 24:
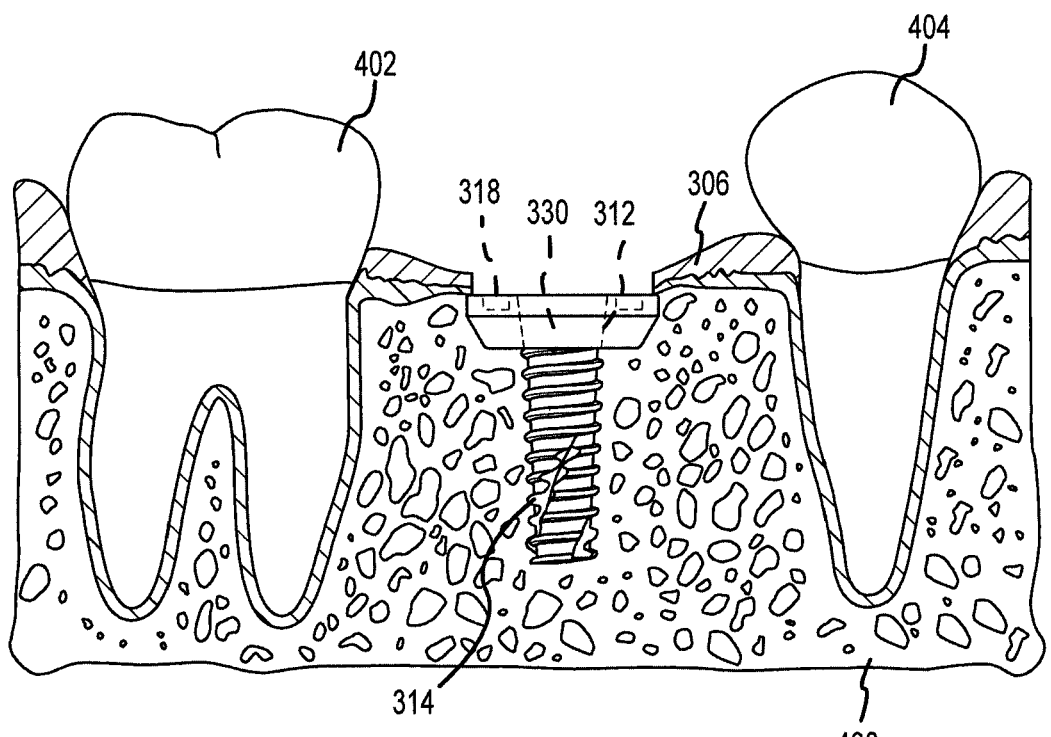
FIG. 24 illustrates an implant screw that has been inserted into the hole of FIG. 23.

As shown in FIG. 23, after base member 302 is in place, a hole is drilled into bone 400 using a drill bit 420 which is passed though central opening 312 of base member 302. Progressively larger drill bits with increasing diameters may be used until the opening in bone 400 is large enough to receive the implant screw. For example, three progressively larger drill bits may be used to form the hole in bone 400. As shown in FIG. 24, implant screw 314 is then inserted through central opening 312 and into the opening in bone 400. Implant screw 314 is tightened until tapered head section 330 is fully seated within central opening 312. A force of around 35 Ncm may be applied with a torque wrench to fully seat implant screw 314 and form a seal that prevents liquids or bacterial from seeping through central opening 312.

Figure 25:
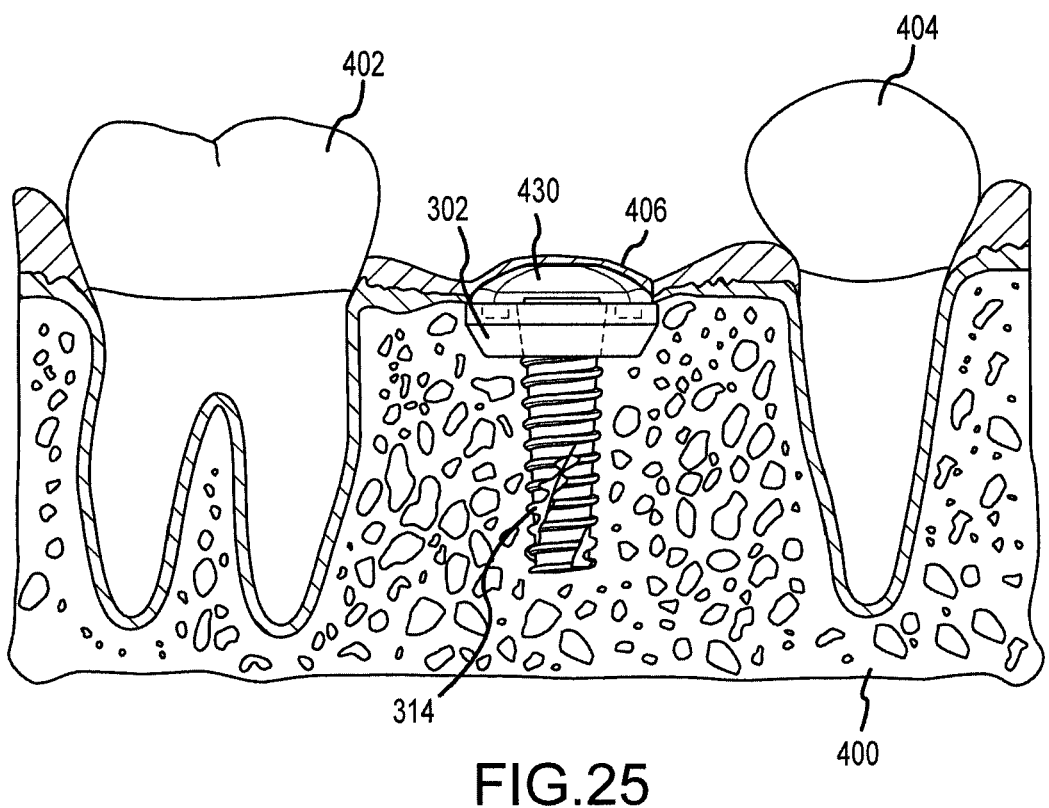
FIG. 25 illustrates a healing cap that has been placed onto the base member after insertion of the implant screw.
Figure 26:
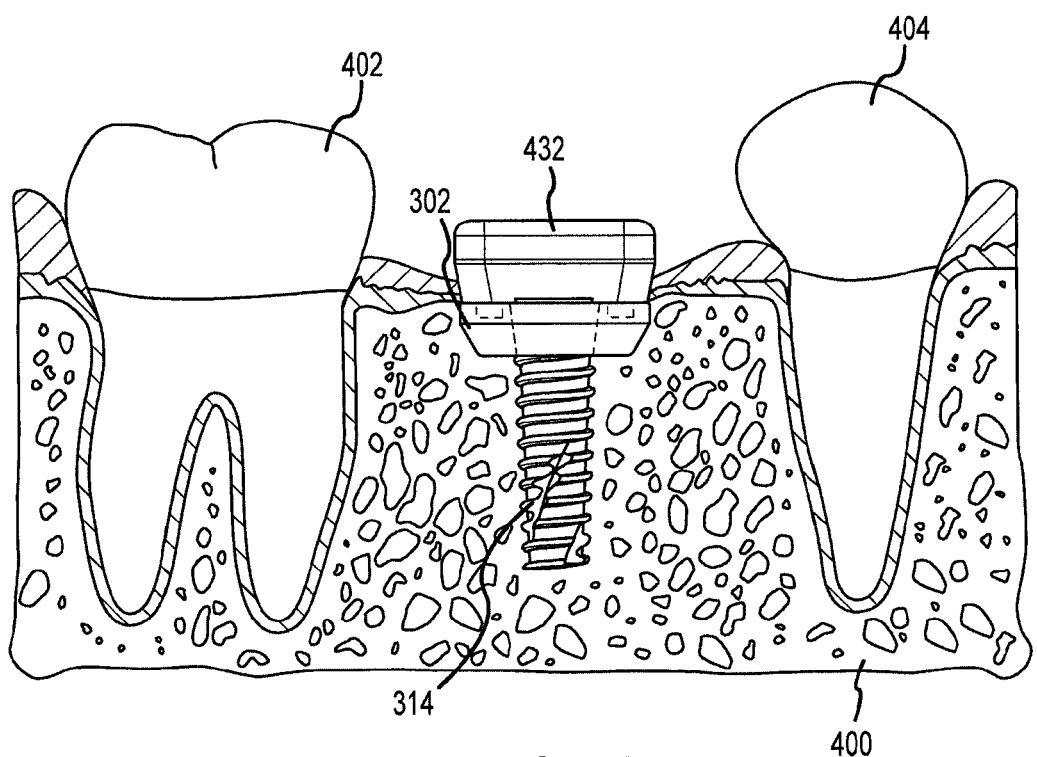
FIG. 26 illustrates a tissue contouring cap that has been placed onto the base member after removal of the healing cap.

As shown in FIG. 25, a healing cover 430 is screwed into opening 332 of implant screw 314. Healing cover 430 is a low profile cover having a maximum height of about 2 mm that extends to the outer periphery of top side 304. Tissue 406 is sutured over cover 430 and left in place for about 3 months while the surgical site heals. When healing is complete, bone integration with base member 302 has occurred and tissue 406 is removed to expose cover 430 which is then removed from base member 302.

A tissue contouring cap 432 (see FIG. 26) is secured to implant screw 314 and base member 302 to form the tissue at the surgical site so that it will be ready to receive the abutment. Tissue contouring cap 432 may be left in place for about 2 weeks, then removed.

Figure 27:
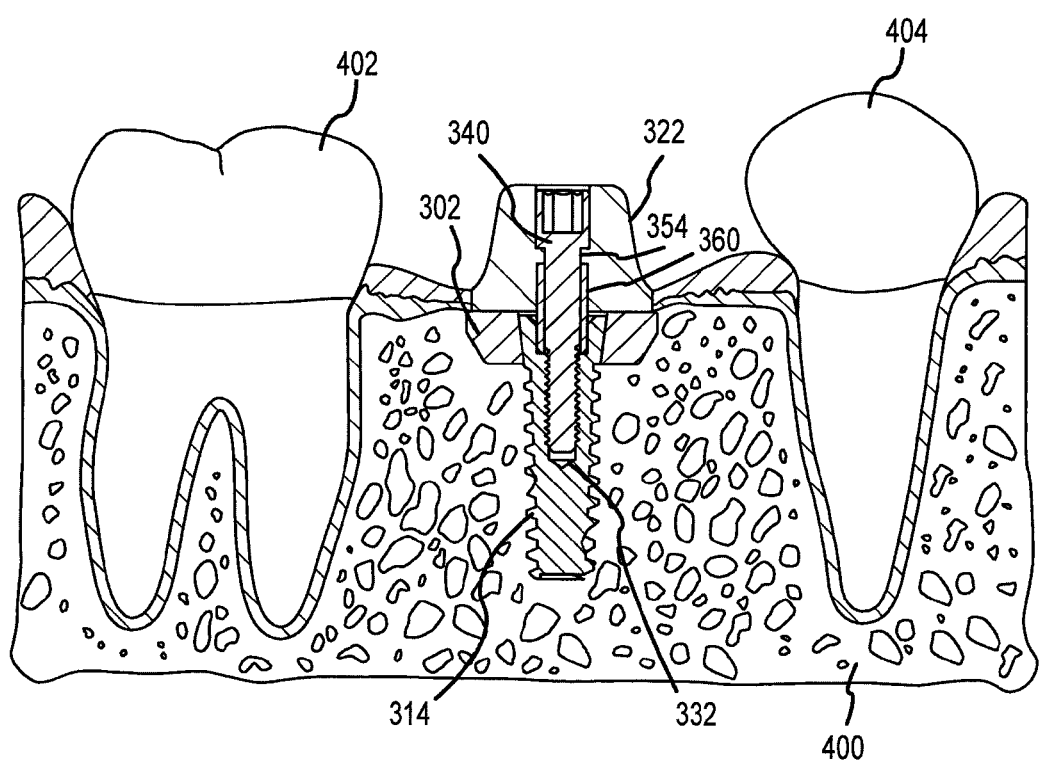
FIG. 27 illustrates the attachment of an abutment to the base member.

Following removal of tissue contouring cap 432, abutment 322 is placed onto base member 302 as shown in FIG. 27. To do so, locating sleeve 360 may be inserted into space 366 and forced into place. Also, alignment pins may be placed into the recess 316 and 318 of base member 302. Abutment is moved toward top side 304, with locating sleeve 360 extending into through hole 354 and pins 320 passing into recesses 323 and 325. Capture screw 340 is inserted through through hole 354 and into opening 332 of implant screw 314. A torque wrench is used to tighten capture screw 340, typically with a force of about 25 Ncm to form a tight seal between abutment 322 and base member 302.

Figure 28:
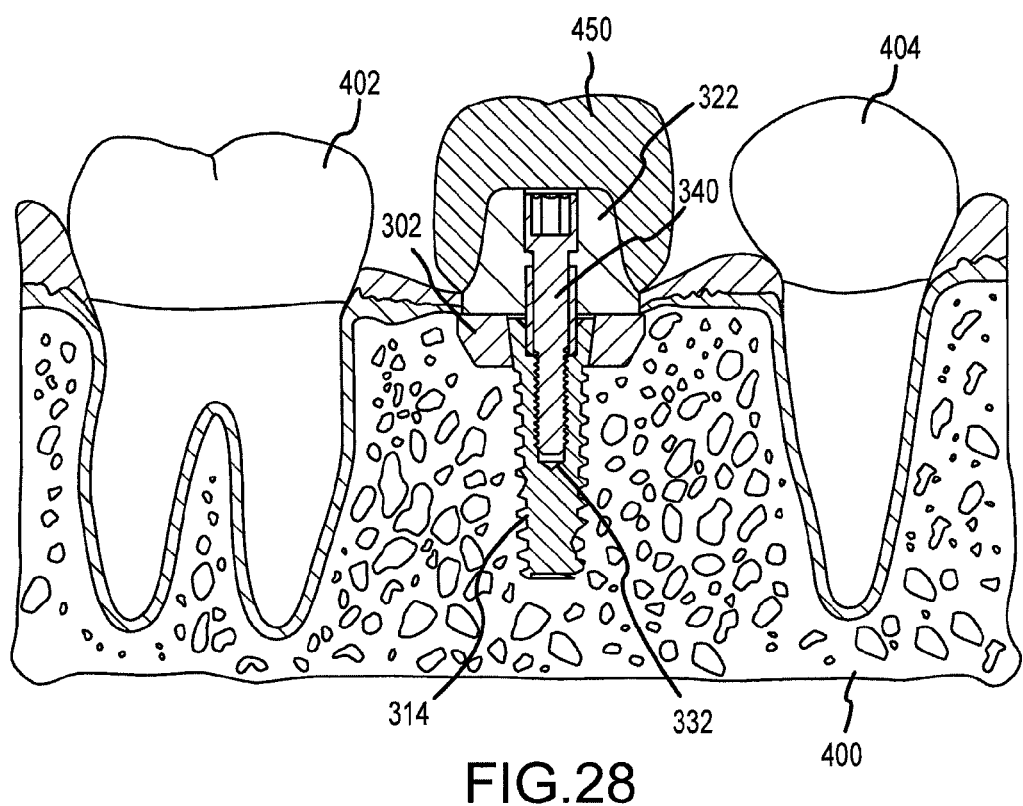
FIG. 28 illustrates the attachment of a crown to the abutment of FIG. 27.

With implant 322 in place, an impression of the crown is made. As shown in FIG. 28, a crown 450 is cemented onto abutment 322.

The foregoing description is only illustrative of the invention and not intended to be exhaustive or to limit the invention to the precise forms disclosed. Various alternatives and modifications can be devised by those skilled in the art without departing from the invention. Accordingly, the present invention embraces all such alternatives, modifications, and variances that fall within the scope of the appended claims.

What is claimed is:

1. A method for securing a dental implant system to a patient's jawbone, the method comprising:
   cutting a portion of the patient's gum at a treatment site sufficient to expose the patient's jawbone;
   positioning a tool over the treatment site, the tool having a through hole therein;
   placing a router through the through hole and using the router to remove a portion of the patient's jawbone at the treatment site to form a recess, wherein the recess is generally square or rectangular in geometry, with four sides and a bottom;
   drilling a generally cylindrical hole with a drill bit into the jawbone at the bottom of the recess;
   positioning a base member that is generally square or rectangular in geometry at the treatment site such that the base member is embedded within the patient's jawbone at the treatment site, wherein the base member has a generally flat top side defined by an outer perimeter, a bottom side and a tapered central opening;
   wherein the drilled cylindrical hole is located in the jawbone so as to be accurately aligned with the central opening in the base member and is generally perpendicular to the bottom of the recess;
   inserting an implant screw through the central opening, wherein the implant screw has a head with a tapered section and a threaded end, and wherein the implant screw is perpendicular to the flat top side of the base member; and
   turning the implant screw to secure the threaded end within the jawbone and to seat the head of the implant screw within the tapered opening of the base member such that the entire bottom side of the base member is in contact with the bottom of the recess.

2. A method as in claim 1, wherein the top side of the base member is generally flush with the patient's jawbone.

3. A method as in claim 1, further comprising placing an abutment onto the top side of the base member, wherein the top side of the base member further includes at least one recess and further comprising placing a locating pin in the recess and inserting the locating pin into a corresponding recess on the abutment when placing the abutment on the base member to ensure non-rotatable alignment of the abutment with the base member.

4. A method as in claim 3, wherein the implant screw includes a threaded hole and further comprising a capture screw, and inserting the capture screw through a central opening of the abutment and into the threaded hole.

5. A method as in claim 4, further comprising seating the implant screw into the jawbone using a tool to adequately engage the tapered section with the tapered opening of the base member.

6. A method as in claim 4, wherein the abutment includes a locating sleeve extending from the central opening of the abutment, and further comprising placing the locating sleeve into the central opening of the base member.

7. A method as in claim 1, further comprising placing a healing cover onto the base member and suturing the patient's gum over the healing cover, wherein the healing cover extends to the outer perimeter of the base member.

8. A method as in claim 7, further comprising accessing the healing cover, removing the healing cover from the base member and placing a tissue contouring cap onto the base member using a screw that extends into the implant screw.

9. A method as in claim 8, further comprising removing the contouring cap and securing an abutment to the base using a capture screw that extends through the abutment and into the implant screw.

10. A method as in claim 9, further comprising attaching a crown to the abutment.

11. A method as in claim 1, wherein the bottom side of the base member is generally flat, wherein the central opening tapers inward from the top side to the bottom side with a constant taper, and wherein the base member has an outer periphery that tapers with a straight taper inward from the top side to the bottom side such that the top side is greater in surface area than the bottom side.

12. A method as in claim 1, wherein the treatment site is where a tooth previously existed, and wherein the base member is sized to be generally the same size as the removed tooth.

13. A method as in claim 1, wherein the outer periphery of the base member includes a coating or surface treatment to increase the surface area of the outer periphery to promote osseointegration.

14. A method as in claim 1, wherein two of the sides of the base member have a length in the range of about 7 mm to about 12 mm, wherein the opposing sides of the base member have a length in the range from about 5 mm to about 10 mm, and wherein the thickness of the base member is in the range from about 1 mm to about 4 mm.

15. A method for securing a dental implant system to a patient's jawbone, the method comprising:
    cutting a portion of the patient's gum at a treatment site sufficient to expose the patient's jawbone;
    removing a portion of the patient's jawbone at the treatment site to form a recess, wherein the recess includes a bottom;
    drilling a generally cylindrical hole with a drill bit into the jawbone at the bottom of the recess, wherein the hole is generally centrally located in the bottom and generally perpendicular to the bottom;
    positioning a base member at the treatment site such that the base member is embedded within the patient's jawbone at the treatment site, wherein the base member has a generally flat top side defined by an outer perimeter, a bottom side and a tapered central opening;
    inserting an implant screw through the central opening, wherein the implant screw has a head with a tapered section and a threaded end; and
    turning the implant screw to secure the threaded end within the hole in the jawbone and to seat the head of the implant screw within the tapered opening of the base member such that the entire bottom side of the base member is in contact with the bottom of the recess, and wherein the implant screw is perpendicular to the flat top side of the base member;
    placing an abutment onto the top surface of the base member, wherein the abutment includes at least one locating pin, wherein the top side of the base member further includes at least one recess, and further comprising placing the locating pin in the recess when placing the abutment on the base member to ensure non-rotatable alignment of the abutment with the base member.

16. A method for securing a dental implant system to a patient's jawbone, the method comprising:
    removing a portion of the patient's gum at a treatment site sufficient to expose the patient's jawbone;
    removing a portion of the patient's jawbone at the treatment site to form a recess;
    positioning a base member at the treatment site such that the base member is embedded within the patient's jawbone at the treatment site, wherein the base member has a generally flat top side defined by an outer perimeter and a tapered central opening;
    placing a drill bit through the central opening and drilling a hole in the jawbone;
    inserting an implant screw through the central opening, wherein the implant screw has a head with a tapered section and a threaded end; and
    turning the implant screw to secure the threaded end within the hole in the jawbone and to seat the head of the implant screw within the tapered opening of the base member;
    placing an abutment onto the top surface of the base member, wherein the top side of the base member further includes at least one recess and further comprising placing a locating pin in the recess and inserting the locating pin into a corresponding recess on the abutment when placing the abutment on the base member to ensure non-rotatable alignment of the abutment with the base member.

17. A method as in claim 16, further comprising placing drill bits of increasing size into the central opening to expand the size of the hole in the jawbone.

18. A method as in claim 16, wherein the drill bit is placed through the central opening.

19. A method for securing a dental implant system to a patient's jawbone, the method comprising:
    cutting a portion of the patient's gum at a treatment site sufficient to expose the patient's jawbone;
    positioning a tool over the treatment site, the tool having a through hole therein;
    placing a router through the through hole and using the router to remove a portion of the patient's jawbone at the treatment site to form a recess, wherein the recess is generally square or rectangular in geometry, with four sides and a bottom;

drilling a generally cylindrical hole with a drill bit into the jawbone at the bottom of the recess;

positioning a base member that is generally square or rectangular in geometry at the treatment site such that the base member is embedded within the patient's jawbone at the treatment site, wherein the base member has a generally flat top side defined by an outer perimeter, a bottom side and a tapered central opening;

wherein the drilled cylindrical hole is located in the jawbone so as to be accurately aligned with the central opening in the base member;

inserting an implant screw through the central opening, wherein the implant screw has a head with a tapered section and a threaded end, and wherein the implant screw is perpendicular to the flat top side of the base member; and turning the implant screw to secure the threaded end within the jawbone and to seat the head of the implant screw within the tapered opening of the base member such that the head of the implant screw seats securely so that the implant screw is perpendicular to a central axis of the central opening in the base member.

* * * * *